(12) United States Patent
Roth et al.

(10) Patent No.: US 6,858,641 B2
(45) Date of Patent: Feb. 22, 2005

(54) SUBSTITUTED INDOLINONES

(75) Inventors: Gerald Juergen Roth, Biberach (DE); Armin Heckel, Biberach (DE); Thorsten Lehmann-Lintz, Ochsenhausen (DE); Joerg Kley, Mittelbiberach (DE); Frank Hilberg, Vienna (AT); Jacobus Van Meel, Moedling (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/116,365

(22) Filed: Apr. 4, 2002

(65) Prior Publication Data

US 2003/0092756 A1 May 15, 2003

(30) Foreign Application Priority Data

Apr. 6, 2001 (DE) .......................................... 101 17 204

(51) Int. Cl.⁷ ........................ A61K 31/40; C07D 209/34
(52) U.S. Cl. ........................ 514/415; 514/418; 548/484; 548/486
(58) Field of Search ................................ 514/415, 418; 548/484, 486

(56) References Cited

U.S. PATENT DOCUMENTS

| 6,043,254 A | 3/2000 | Grell et al. | |
|---|---|---|---|
| 6,169,106 B1 | 1/2001 | Heckel et al. | |
| 6,319,918 B1 | * 11/2001 | Heckel et al. | ......... 514/213.01 |

FOREIGN PATENT DOCUMENTS

| DE | 198 24 922 A1 | 12/1999 | |
|---|---|---|---|
| DE | 199 40 829 | 3/2001 | |
| DE | 100 42 696 | 3/2002 | |
| WO | WO 98 07695 A | 2/1998 | |
| WO | WO 99 15500 A | 4/1999 | |
| WO | WO 9915500 A1 * | 4/1999 | ......... C07D/209/40 |
| WO | WO 99/52869 | 10/1999 | |
| WO | WO 99/62882 | 12/1999 | |
| WO | WO 00/73297 | 12/2000 | |
| WO | WO 01/16130 | 3/2001 | |
| WO | WO 01/27081 | 4/2001 | |

OTHER PUBLICATIONS

Stein, J. H. et al., Editor–in–Chief, Internal Medicine, 4th Edition, Chapters 71 and 72, 1994.*

Roth, G. J. et al, U.S. Appl. No. 10/069,557, filed Jul. 22, 2002, "New Substituted Indolinones, Their Manufacture and Their Use As Medicaments".

Roth, G. J. et al, U.S. Appl. No. 09/678,682, filed Oct. 3, 2000, "Substituted Indolines Which Inhibit Receptor Tyrosine Kinases".

* cited by examiner

*Primary Examiner*—Dwayne C. Jones
(74) *Attorney, Agent, or Firm*—Robert P. Raymond; Michael P. Morris; Philip I. Datlow

(57) ABSTRACT

The present invention relates to indolinones substituted in the 6-position of general formula (I)

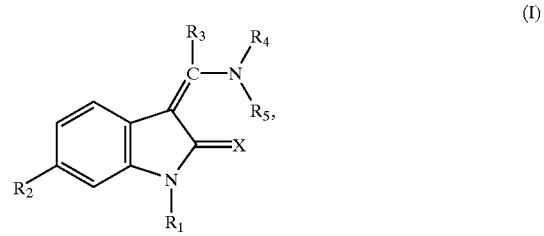

wherein
$R_1$ to $R_5$ and X are defined as in claim 1, the isomers and the salts thereof, particularly the physiologically acceptable salts thereof which have valuable pharmacological properties, in particular an inhibiting effect on various receptor tyrosine kinases and cyclin/CDK complexes and on the proliferation of endothelial cells and various, pharmaceutical compositions containing these compounds, their use and processes for preparing them.

9 Claims, No Drawings

SUBSTITUTED INDOLINONES

The present invention relates to new indolinones substituted in the 6-position of general formula

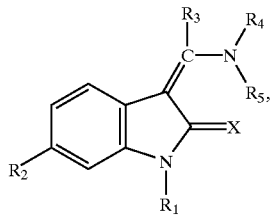

(I)

the tautomers, diastereomers, enantiomers and mixtures thereof and the salts thereof, particularly the physiologically acceptable salts thereof which have valuable properties.

The above compounds of general formula I wherein $R_1$ denotes a hydrogen atom or a prodrug group have valuable pharmacological properties, in particular an inhibiting effect on various kinases, especially receptor tyrosine kinases such as VEGFR2, VEGFR3, PDGFRα, PDGFRβ, FGFR1, FGFR3, EGFR, HER2, IGF1R and HGFR, as well as complexes of CDK's (Cyclin Dependent Kinases) such as CDK1, CDK2, CDK3, CDK4, CDK5, CDK6, CDK7, CDK8 and CDK9 with their specific cyclins (A, B 1, B2, C, D1, D2, D3, E, F, G1, G2, H, I and K) and on viral cyclin (cf. L. Mengtao in J. Virology 71(3), 1984–1991 (1997)), on the proliferation of cultivated human cells, in particular endothelial cells, e.g. in angiogenesis, but also on the proliferation of other cells, in particular tumour cells.

The other compounds of the above general formula I wherein $R_1$ does not denote a hydrogen atom or a prodrug group are valuable intermediate products for preparing the abovementioned compounds.

The present invention thus relates to the above compounds of general formula I, whilst those compounds wherein $R_1$ denotes a hydrogen atom or a prodrug group have valuable pharmacological properties, pharmaceutical compositions containing the pharmacologically active compounds, the use thereof and processes for preparing them.

In the above general formula I

X denotes an oxygen or sulphur atom, $R_1$ denotes a hydrogen atom or a group which can be cleaved in vivo such as a $C_{1-4}$-alkoxycarbonyl or $C_{2-4}$-alkanoyl group, $R_2$ denotes a carboxy group, a straight-chain or branched $C_{1-6}$-alkoxycarbonyl group, a $C_{4-7}$-cycloalkoxycarbonyl or an aryloxycarbonyl group, $R_3$ denotes a hydrogen atom, a $C_{1-6}$-alkyl, $C_{3-7}$-cycloalkyl, trifluoromethyl or heteroaryl group, a phenyl or naphthyl group, or a phenyl or naphthyl group mono- or disubstituted by a fluorine, chlorine, bromine or iodine atom, by a trifluoromethyl, $C_{1-3}$-alkyl or $C_{1-3}$-alkoxy group, while in the event of disubstitution the substituents may be identical or different, $R_4$ denotes a phenyl, pyrrolyl or furanyl group substituted by the group $R_6$, which may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and wherein $R_6$ denotes an aminocarbonyl, $C_{1-4}$-alkylamino-carbonyl, N—($C_{1-5}$-alkyl)-N—$C_{1-3}$-alkyl-aminocarbonyl, $C_{3-7}$-cycloalkylamino-carbonyl, N—($C_{1-5}$-alkyl)-N—$C_{3-7}$-cycloalkylamino-carbonyl, (phenyl-$C_{1-3}$-alkyl)amino-carbonyl, N—($C_{1-3}$-alkyl)-N-phenyl-$C_{1-3}$-alkylamino-carbonyl group, a $C_{1-3}$-alkylaminocarbonyl or N—($C_{1-3}$-alkyl)-N—$C_{1-3}$-alkylaminocarbonyl group wherein one or two alkyl moieties are substituted independently of one another by a nitro, cyano, carbamoyl, N—($C_{1-3}$-alkyl)-carbamoyl, di-N—($C_{1-3}$-alkyl)-carbamoyl, carboxy or $C_{1-3}$-alkoxycarbonyl group or are substituted in the 2- or 3-position by an amino, ($C_{1-3}$-alkyl)-amino, di-($C_{1-3}$-alkyl)-amino, ($C_{1-4}$-alkoxycarbonyl)-amino, N—($C_{1-4}$-alkoxycarbonyl)-N—($C_{1-3}$-alkyl)-amino, piperazino, N—($C_{1-3}$-alkyl)-piperazino, a 4- to 7-membered cycloalkyleneimino group, a hydroxy or methoxy group, a 4- to 7-membered cycloalkyleneiminocarbonyl group wherein the cycloalkylene moiety may be fused to a phenyl ring via two adjacent ring atoms or may form a bridge to a methylene or ethylene group via two non-adjacent ring atoms or one or two hydrogen atoms may each be replaced by a $C_{1-3}$-alkyl group and/or in each case the methylene group in the 4 position of a 6- or 7-membered cyclo-alkyleneiminocarbonyl group may be substituted by a carboxy, $C_{1-4}$-alkoxycarbonyl, aminocarbonyl, $C_{1-3}$-alkylaminocarbonyl, di-($C_{1-3}$-alkyl)-aminocarbonyl, di-($C_{1-3}$-alkyl)-amino-$C_{1-3}$-alkyl, di-($C_{1-3}$-alkyl)-amino, phenyl-$C_{1-3}$-alkylamino or N—($C_{1-3}$-alkyl)-N-phenyl-$C_{1-3}$-alkylamino group, a hydroxy or methoxy group or may be replaced by an oxygen or sulphur atom, by a sulphinyl, sulphonyl or —NH group or by a nitrogen atom which is substituted by a $C_{1-3}$-alkyl, phenyl, $C_{1-3}$-alkyl-carbonyl, $C_{1-4}$-alkoxy-carbonyl, di-($C_{1-3}$-alkyl)-amino-$C_{1-3}$-alkyl, ω-hydroxy-$C_{2-3}$-alkyl or benzoyl group, while all the single-bonded or fused phenyl groups contained in the groups mentioned under $R_6$ may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, while the substituents may be identical or different, or two adjacent hydrogen atoms of the phenyl groups may be replaced by a methylenedioxy group, and $R_5$ denotes a hydrogen atom or a $C_{1-3}$-alkyl group, while by the term aryl group is meant a phenyl or naphthyl group optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and by the term heteroaryl group is meant a monocyclic 5- or 6-membered heteroaryl group optionally substituted in the carbon skeleton by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bond is via a nitrogen atom or via a carbon atom of the heterocyclic moiety of a fused phenyl ring, the hydrogen atoms in the abovementioned alkyl and alkoxy groups or in the alkyl moieties contained in the above-defined groups of formula I may be wholly or partly replaced by fluorine atoms, the saturated alkyl and alkoxy moieties containing more than 2 carbon atoms present in the groups defined above, also include the branched isomers thereof such as for example the isopropyl, tert.butyl, isobutyl group, unless otherwise stated, and wherein additionally the hydrogen atom of any carboxy group present or a hydrogen atom bound to a nitrogen atom, for example an amino, alkylamino or imino group or a saturated N-heterocycle such as the piperidinyl group, may be replaced in each case by a group which can be cleaved in vivo, the tautomers, diastereomers, enantiomers and mixtures thereof and the salts thereof.

By a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl groups, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_eCO$—$O$—$(R_fCR_g)$—$O$—$CO$ group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_eCO$—$O$—$(R_fCR_g)$—$O$ group wherein $R_e$ to $R_g$ are as hereinbefore defined, wherein additionally the amino group may be a phthalimido group, while the ester groups mentioned above may also be used as a group which can be converted in vivo into a carboxy group.

An essential feature of the present invention is that $R_6$ denotes an unsubstituted aminocarbonyl group or an aminocarbonyl group which is substituted as defined hereinbefore or hereinafter.

Preferred compounds of general formula I are those wherein

X denotes an oxygen atom, $R_1$ denotes a hydrogen atom, a $C_{1-4}$-alkoxycarbonyl or $C_{2-4}$-alkanoyl group, $R_2$ denotes a carboxy group or a straight-chain or branched $C_{1-4}$-alkoxycarbonyl group, $R_3$ denotes a hydrogen atom, a $C_{1-6}$-alkyl or $C_{3-7}$-cycloalkyl group, a phenyl or naphthyl group, or a phenyl or naphthyl group mono- or disubstituted by a fluorine, chlorine or bromine atom, by a trifluoromethyl, $C_{1-3}$-alkyl or $C_{1-3}$-alkoxy group, while in the case of disubstitution the substituents may be identical or different, $R_4$ denotes a furanyl group substituted by an aminocarbonyl, $C_{1-4}$-alkylaminocarbonyl or N—($C_{1-4}$-alkyl)-N—$C_{1-3}$-alkylaminocarbonyl group, wherein the $C_{1-4}$-alkylaminocarbonyl or N—($C_{1-4}$-alkyl)-N—$C_{1-3}$-alkylaminocarbonyl group may be substituted from position 2 in one or both alkyl moieties by an amino, $C_{1-3}$-alkylamino or di-($C_{1-3}$-alkyl)amino group, a pyrrolyl group substituted by an aminocarbonyl, $C_{1-4}$-alkylaminocarbonyl or N—($C_{1-4}$-alkyl)-N—$C_{1-3}$-alkylaminocarbonyl group, wherein the $C_{1-4}$-alkylaminocarbonyl or N—($C_{1-4}$-alkyl)-N—$C_{1-3}$-alkylaminocarbonyl group may be substituted from position 2 in one or both alkyl moieties by an amino, $C_{1-3}$-alkylamino or di-($C_{1-3}$-alkyl)amino group and the nitrogen atom of the pyrrolyl ring is optionally substituted by a $C_{1-3}$-alkyl group, or a phenyl group substituted by the group $R_6$, which may additionally be mono- or disubstituted by fluorine, chlorine or bromine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and wherein $R_6$ denotes an aminocarbonyl, $C_{1-4}$-alkylamino-carbonyl, N—($C_{1-5}$-alkyl)-N—$C_{1-3}$-alkyl-aminocarbonyl, $C_{3-7}$-cycloalkylamino-carbonyl, N—($C_{1-5}$-alkyl)-N—$C_{3-7}$-cycloalkylamino-carbonyl, (phenyl-$C_{1-3}$-alkyl)aminocarbonyl, N—($C_{1-3}$-alkyl)-N-phenyl-$C_{1-3}$-alkyl-aminocarbonyl group, a $C_{1-3}$-alkylaminocarbonyl or N—($C_{1-3}$-alkyl)-N—$C_{1-3}$-alkylaminocarbonyl group wherein one or two alkyl moieties are substituted independently of one another by a nitro, cyano, carbamoyl, N—($C_{1-3}$-alkyl)-carbamoyl, di-N—($C_{1-3}$-alkyl)-carbamoyl, carboxy or $C_{1-3}$-alkoxycarbonyl group or are substituted in the 2- or 3-position by an amino, ($C_{1-3}$-alkyl)-amino, di-($C_{1-3}$-alkyl)-amino, ($C_{1-4}$-alkoxycarbonyl)-amino, N—($C_{1-4}$-alkoxycarbonyl)-N—($C_{1-3}$-alkyl)-amino, piperazino, N—($C_{1-3}$-alkyl)-piperazino, a piperazinyl or piperidinyl group, a hydroxy or methoxy group, a 4- to 7-membered cycloalkyleneiminocarbonyl group wherein the cycloalkylene moiety may be fused to a phenyl ring via two adjacent ring atoms or via two non-adjacent ring atoms may form a bridge to a methylene or ethylene group or one or two hydrogen atoms may each be replaced by a $C_{1-3}$-alkyl group and/or in each case the methylene group in the 4 position of a 6- or 7-membered cycloalkyleneiminocarbonyl group may be substituted by a carboxy, $C_{1-4}$-alkoxycarbonyl, aminocarbonyl, $C_{1-3}$-alkylaminocarbonyl, di-($C_{1-3}$-alkyl)-aminocarbonyl, di-($C_{1-3}$-alkyl)-amino-$C_{1-3}$-alkyl, di-($C_{1-3}$-alkyl)-amino, phenyl-$C_{1-3}$-alkylamino or N—($C_{1-3}$-alkyl)-N-phenyl-$C_{1-3}$-alkylamino group, a hydroxy or methoxy group or may be replaced by an oxygen or sulphur atom, by a sulphinyl, sulphonyl or —NH group or by a nitrogen atom, which is substituted by a $C_{1-3}$-alkyl, phenyl, $C_{1-3}$-alkyl-carbonyl, $C_{1-4}$-alkoxy-carbonyl, di-($C_{1-3}$-alkyl)-amino-$C_{1-3}$-alkyl, ω-hydroxy-$C_{2-3}$-alkyl or benzoyl group, and $R_5$ denotes a hydrogen atom or a $C_{1-3}$-alkyl group, wherein the hydrogen atoms in the abovementioned alkyl and alkoxy groups or in the alkyl moieties contained in the above-defined groups of formula I may be wholly or partly replaced by fluorine atoms, the saturated alkyl and alkoxy moieties containing more than 2 carbon atoms present in the groups defined above also include the branched isomers thereof such as for example the isopropyl, tert.butyl, isobutyl group, unless otherwise stated, and additionally the hydrogen atom of any carboxy group present or a hydrogen atom bound to a nitrogen atom, for example an amino, alkylamino or imino group or a saturated N-heterocycle such as the piperidinyl group, may be replaced in each case by a group which can be cleaved in vivo, the tautomers, diastereomers, enantiomers and mixtures thereof and the salts thereof.

A preferred sub-group relates to compounds of general formula I wherein

X denotes an oxygen atom, $R_1$ denotes a hydrogen atom, $R_2$ denotes a carboxy group or a $C_{1-2}$-alkoxycarbonyl group, $R_3$ denotes a phenyl or naphthyl group, or a phenyl group monosubstituted by a fluorine, chlorine or bromine atom, by a trifluoromethyl, $C_{1-3}$-alkyl or $C_{1-3}$-alkoxy group, $R_4$ denotes a pyrrolyl group substituted by an aminocarbonyl, $C_{1-4}$-alkylaminocarbonyl or N—($C_{1-4}$-alkyl)-N—$C_{1-3}$-alkylaminocarbonyl group, wherein the $C_{1-4}$-alkylaminocarbonyl or N—($C_{1-4}$-alkyl)-N—$C_{1-3}$-alkylaminocarbonyl group may be substituted from position 2 in one or both alkyl moieties by an amino, $C_{1-3}$-alkylamino or di-($C_{1-3}$-alkyl)amino group and the nitrogen atom of the pyrrolyl ring is optionally substituted by a $C_{1-3}$-alkyl group, or a phenyl group substituted in the 3- or 4-position by the group $R_6$, wherein $R_6$ denotes an aminocarbonyl, $C_{1-4}$-alkylamino-carbonyl, N—($C_{1-3}$-alkyl)-N—$C_{1-3}$-alkyl-aminocarbonyl, $C_{5-6}$-cycloalkylamino-carbonyl, N—($C_{1-5}$-alkyl)-N—$C_{5-6}$-cycloalkylamino-carbonyl group, a $C_{1-3}$-alkylaminocarbonyl or N—($C_{1-3}$-alkyl)-N—$C_{1-3}$-alkylaminocarbonyl group wherein one or two alkyl moieties are substituted independently of one another by a carbamoyl, N—($C_{1-3}$-alkyl)-carbamoyl, di-N—($C_{1-3}$-alkyl)-carbamoyl, $C_{1-3}$-alkoxycarbonyl group or are substituted in the 2- or 3-position by an amino, ($C_{1-3}$-alkyl)-amino, di-($C_{1-3}$-alkyl)-amino, ($C_{1-4}$-alkoxycarbonyl)-amino, N—($C_{1-4}$-alkoxycarbonyl)-N—($C_{1-3}$-alkyl)-amino, piperazino, N—($C_{1-3}$-alkyl)-piperazino, a piperazinyl or piperidinyl group, a hydroxy or methoxy group, a piperidinocarbonyl, piperazinocarbonyl, homopiperazinocarbonyl or 2,3,4,5-tetrahydro-1(H)-azepino-carbonyl group, which may be fused to a phenyl ring via two adjacent unsubstituted carbon atoms or may be substituted in the 4 position by a $C_{1-3}$-alkyl, $C_{1-4}$-alkoxycarbonyl, di-($C_{1-3}$-alkyl)-amino, di-($C_{1-3}$-alkyl)-amino-$C_{1-3}$-alkyl, 2-hydroxy-ethyl, hydroxy or methoxy group, or a 2,5-diaza-bicyclo[2.2.1]hept-2-yl-carbonyl group which may be substituted in the 5 position by a $C_{1-3}$-alkyl group, and $R_5$ denotes a hydrogen atom or a $C_{1-3}$-alkyl group, wherein the hydrogen atoms in the abovementioned methyl and methoxy groups may be replaced by 1, 2 or 3 fluorine atoms, and the saturated alkyl and alkoxy moieties containing more than 2 carbon atoms which are present in the groups defined above also include the branched isomers thereof, such as, for example, the isopropyl, tert.butyl and isobutyl group, the tautomers, diastereomers, enantiomers and mixtures thereof and the salts thereof.

Particularly preferred compounds of general formula I are those wherein

X denotes an oxygen atom, $R_1$ and $R_5$ each denote a hydrogen atom, $R_2$ denotes a methoxycarbonyl group, $R_3$ denotes a phenyl group and $R_4$ denotes a phenyl group which is monosubstituted in the 3- or 4-position by the group $R_6$, wherein $R_6$ denotes an aminocarbonyl, $C_{1-3}$-alkylamino-carbonyl, N—($C_{1-5}$-alkyl)-N—$C_{1-3}$-alkyl-aminocarbonyl, cyclohexylaminocarbonyl, N—($C_{1-5}$-alkyl)-N-cyclohexylaminocarbonyl, phenyl-$C_{1-3}$-alkylamino-carbonyl, N—($C_{1-3}$-alkyl)-N-phenyl-$C_{1-3}$-alkylamino-carbonyl, a piperidinocarbonyl, 4-hydroxy-piperidinocarbonyl, 4-[di-($C_{1-3}$-alkyl)-amino]-piperidinocarbonyl, 4-[di-($C_{1-3}$-alkyl)-amino-$C_{1-3}$-alkyl]-piperidinocarbonyl, piperazinocarbonyl, N—($C_{1-3}$-alkyl)-piperazinocarbonyl, N—($C_{1-4}$-alkoxycarbonyl)-piperazinocarbonyl, N-[di-($C_{1-3}$-alkyl)-amino-$C_{1-3}$-alkyl]-piperazinocarbonyl, N-(2-hydroxy-ethyl)-piperazinocarbonyl, homopiperazinocarbonyl, N—($C_{1-3}$-alkyl)-homopiperazinocarbonyl, 2,3,4,5-tetrahydro-1(H)-benzo[d]azepino-carbonyl or 5-methyl-2,5-diaza-bicyclo[2.2.1]hept-2-yl-carbonyl group, a $C_{1-3}$-alkylaminocarbonyl or N—($C_{1-5}$-alkyl)-N—$C_{1-3}$-alkylaminocarbonyl group wherein one or two alkyl moieties are substituted by a carbamoyl group or are substituted in the 2-or 3-position by an amino, ($C_{1-3}$-alkyl)-amino, di-($C_{1-3}$-alkyl)-amino, hydroxy or methoxy group, the tautomers, diastereomers, enantiomers and mixtures thereof and the salts thereof.

The following are mentioned as examples of most particularly preferred compounds:

(a) methyl 3-(Z)-[1-{4-[N-(2-dimethylamino-ethyl)-N-methyl-carbamoyl]-phenylamino}-1-phenyl-methylidene]-2-indolinone-6-carboxylate (b) methyl 3-(Z)-[1-{4-[N-(3-dimethylamino-propyl)-N-methyl-carbamoyl]-phenylamino}-1-phenyl-methylidene]-2-indolinone-6-carboxylate (c) methyl 3-(Z)-[1-{4-[(4-methyl-piperazin-1-yl)-carbonyl]-phenylamino}-1-phenyl-methylidene]-2-indolinone-6-carboxylate (d) methyl 3-(Z)-[1-{4-[(4-hydroxy-piperidin-1-yl)-carbonyl]-phenylamino}-1-phenyl-methylidene]-2-indolinone-6-carboxylate (e) methyl 3-(Z)-[1-{4-[(piperazin-1-yl)-carbonyl]-phenylamino}-1-phenyl-methylidene]-2-indolinone-6-carboxylate (f) methyl 3-(Z)-[1-{4-[N-(2-methylamino-ethyl)-N-methyl-carbamoyl]-phenylamino}-1-phenyl-methylidene]-2-indolinone-6-carboxylate (g) methyl 3-(Z)-[1-{4-[(4-dimethylamino-piperidin-1-yl)-carbonyl]-phenylamino}-1-phenyl-methylidene]-2-indolinone-6-carboxylate (h) methyl 3-(Z)-[1-{4-[(4-ethyl-piperazin-1-yl)-carbonyl]-phenylamino}-1-phenyl-methylidene]-2-indolinone-6-carboxylate (i) methyl 3-(Z)-[1-{4-[(4-(2-hydroxy-ethyl)-piperazin-1-yl)-carbonyl]-phenylamino}-1-phenyl-methylidene]-2-indolinone-6-carboxylate (k) methyl 3-(Z)-{1-[4-(5-methyl-2,5-diaza-bicyclo[2.2.1]hept-2-yl-carbonyl)-phenylamino]-1-phenyl-methylidene}-2-indolinone-6-carboxylate the tautomers, mixtures and salts thereof.

According to the invention, the new compounds are obtained, for example, using the following methods known in principle from the literature:

a. reacting a compound of general formula

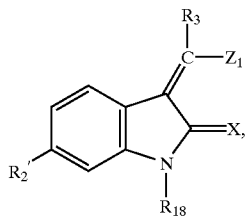

(VII)

wherein

X and $R_3$ are as hereinbefore defined, $R_2'$ has the meanings given for $R_2$ hereinbefore, $R_{18}$ denotes a hydrogen atom or a protecting group for the nitrogen atom of the lactam group, wherein one of the groups $R_2'$ and $R_{18}$ may also denote a bond to a solid phase optionally formed via a spacer and the other of the groups $R_2'$ and $R_{18}$ has the meanings given hereinbefore, and $Z_1$ denotes a halogen atom, a hydroxy, alkoxy or aryl-alkoxy group, e.g. a chlorine or bromine atom, a methoxy, ethoxy or benzyloxy group, with an amine of general formula

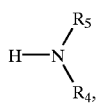

(VIII)

wherein $R_4$ and $R_5$ are as hereinbefore defined, and if necessary subsequently cleaving any protecting group used for the nitrogen atom of the lactam or imino group or from a solid phase.

A protecting group for the nitrogen atom of the lactam group might be for example an acetyl, benzoyl, ethoxycarbonyl, tert.butyloxycarbonyl or benzyloxycarbonyl group and the solid phase might be a resin such as a 4-(2',4'-dimethoxyphenylaminomethyl)-phenoxy resin, whilst the bond may conveniently be formed via the amino group, or a p-benzyloxybenzylalcohol resin, whilst the bond may conveniently be formed via an intermediate member such as a 2,5-dimethoxy-4-hydroxy-benzyl derivative.

The reaction is conveniently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., whilst any protecting group used can be cleaved simultaneously by transamidation.

If $Z_1$ in a compound of general formula VII denotes a halogen atom, the reaction is preferably carried out in the presence of an inert base at temperatures between 20 and 120° C.

If $Z_1$ in a compound of general formula VII denotes a hydroxy, alkoxy or aralkoxy group, the reaction is preferably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with an organic base such as ammonia, butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

Any solid phase used is preferably cleaved using trifluoroacetic acid and water at temperatures between 0 and 35° C., preferably at ambient temperature.

b. In order to prepare a compound of general formula I wherein $R_2$ has the meanings given hereinbefore with the exception of the carboxy group:

reacting a compound of general formula

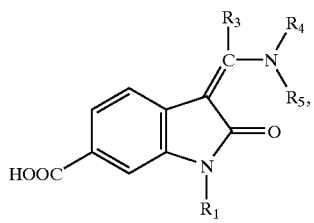

(IX)

wherein $R_1$ and $R_3$ to $R_5$ are as hereinbefore defined, or the reactive derivatives thereof with a compound of general formula

(X), wherein $R_{19}$ denotes a straight-chain or branched $C_{1-6}$-alkanol, a $C_{4-7}$-cycloalkanol or an aromatic alcohol.

The esterification is preferably carried out in a solvent such as methylene chloride, diethyl ether, tetrahydrofuran, toluene, dioxane, acetonitrile, dimethylsulphoxide or dimethylformamide, optionally in the presence of an inorganic or tertiary organic base, is preferably at temperatures between 20° C. and the boiling temperature of the solvent used. The reaction is carried out with a corresponding acid, preferably in the presence of a dehydrating agent, e.g. in the presence of isobutyl chloroformate, thionyl chloride, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexyl carbodiimide/N-hydroxysuccinimide, N,N'-dicyclohexyl carbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluooborate/1-hydroxybenotriazole, N,N'-carbonyldiimidazole or triphenylphosphine/carbon tetrachloride, and optionally with the addition of a base such as pyridine, 4-dimethylaminopyridine, N-methyl-morpholine or triethylamine, expediently at temperatures between 0 and 150° C., preferably at temperatures between 0 and 100° C., and the acylation is carried out with a corresponding reactive compound such as the anhydride, ester, imidazolide or halide thereof, optionally in the presence of a tertiary organic base such as triethylamine, N-ethyl-diisopropylamine or N-methyl-morpholine at temperatures between 0 and 150° C., preferably at temperatures between 50 and 100° C.

If according to the invention a compound of general formula I is obtained which contains an alkoxycarbonyl group, this can be converted by hydrolysis into a corresponding carboxy compound, or if a compound of general formula I is obtained which contains an amino or alkylamino group, this may be converted by reductive alkylation into a corresponding alkylamino or dialkylamino compound, or if a compound of general formula I is obtained which contains an amino or alkylamino group, this may be converted by acylation or sulphonylation into a corresponding acyl or sulphonyl compound, or if a compound of general formula I is obtained which contains a carboxy group, this may be converted by esterification or amidation into a corresponding ester or aminocarbonyl compound, or if a compound of general formula I is obtained which contains a cycloalkyleneimino group wherein a methylene group is replaced by a sulphur atom, this may be converted by oxidation into a corresponding sulphinyl or sulphonyl compound, or if a compound of general formula I is obtained which contains a nitro group, this may be converted by reduction into a corresponding amino compound, or if a compound of general formula I is obtained wherein $R_4$ denotes a phenyl group substituted by an amino, alkylamino or aminoalkyl group, this may subsequently be converted by reacting with a corresponding cyanate, isocyanate or carbamoyl halide into a corresponding urea compound of general formula I or if a compound of general formula I is obtained wherein $R_4$ denotes a phenyl group substituted by an amino, alkylamino or aminoalkyl group, this may subsequently be converted by reacting with a corresponding compound which transfers the amidino group or by reacting with a corresponding nitrile into a corresponding guanidino compound of general formula I.

The subsequent hydrolysis is preferably carried out in an aqueous solvent, e.g. in water, methanol/water, ethanol/water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxane, methylene chloride or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, sodium cyanoborohydride, lithium borohydride or lithium aluminium hydride at temperatures between 0 and 100° C., preferably at temperatures between 20 and 80° C.

The subsequent acylation or sulphonylation is conveniently carried out with the corresponding free acid or a corresponding reactive compound such as an anhydride, ester, imidazolide or halide thereof, preferably in a solvent such as methylene chloride, diethyl ether, tetrahydrofuran, toluene, dioxane, acetonitrile, dimethylsulphoxide or dimethylformamide, optionally in the presence of an inorganic or a tertiary organic base, preferably at temperatures between −20° C. and 200° C., preferably at temperatures between 20° C. and the boiling temperature of the solvent used. The reaction with the free acid may optionally be carried out in the presence of an acid activating agent or a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C. The reaction with a corresponding reactive compound may optionally be carried out in the presence of a tertiary organic base such as triethylamine, N-ethyl-diisopropylamine, N-methyl-morpholine or pyridine, or, if an anhydride is used, in the presence of the corresponding acid, at temperatures between 0 and 150° C., preferably at temperatures between 50 and 100° C.

The subsequent esterification or amidation is expediently carried out by reacting a corresponding reactive carboxylic acid derivative with a corresponding alcohol or amine as described hereinbefore.

The subsequent reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

The subsequent preparation of a corresponding urea compound of general formula I is conveniently carried out with an inorganic cyanate or a corresponding isocyanate or carbamoylchloride, preferably in a solvent such as dimethylformamide and optionally in the presence of a tertiary organic base such as triethylamine at temperatures between 0 and 50° C., preferably at ambient temperature.

The subsequent preparation of a corresponding guanidino compound of general formula I is conveniently carried out by reacting with a compound that transfers the amidino group, such as 3,5-dimethylpyrazol-1-carboxylic acid amidine, preferably in a solvent such as dimethylformamide and optionally in the presence of a tertiary organic base such as triethylamine at temperatures between 0 and 50° C., preferably at ambient temperature.

In the reactions described hereinbefore, any reactive groups present such as carboxy, hydroxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for a hydroxy, amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of a acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, chiral compounds obtained of general formula I may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be, for example, (+)- or (−)-menthol and an optically active acyl group in amides may be, for example, a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae VII to X used as starting materials are known from the literature in some cases or may be obtained by methods known from the literature or may be obtained by methods as described hereinbefore and in the Examples.

As already mentioned, the new compounds of general formula I wherein $R_1$ denotes a hydrogen atom or a prodrug group have valuable pharmacological properties, particularly inhibitory effects on various kinases, especially on receptor-tyrosine kinases such as VEGFR2, VEGFR3, PDGFRα, PDGFRβ, FGFR1, FGFR3, EGFR, HER2, IGF1R and HGFR, as well as on complexes of CDK's (Cyclin Dependent Kinases) such as CDK1, CDK2, CDK3, CDK4, CDK5, CDK6, CDK7, CDK8 and CDK9 with their specific cyclins (A, B1, B2, C, D1, D2, D3, E, F, G1, G2, H, I and K) and on viral cyclin, on the proliferation of cultivated human cells, particularly endothelial cells, e.g. in angiogenesis, but also on the proliferation of other cells, particularly tumour cells.

The biological properties of the new compounds were tested by the following standard procedure, as follows:

Human umbilical endothelial cells (HUVEC) were cultivated in IMDM (Gibco BRL), supplemented with 10% foetal calf serum (FBS) (Sigma), 50 µM of β-mercaptoethanol (Fluka), standard antibiotics, 15 µg/ml of endothelial cell growth factor (ECGS, Collaborative Biomedical Products) and 100 µg/ml of heparin (Sigma) on gelatine-coated culture dishes (0.2% gelatine, Sigma) at 37° C., under 5% $CO_2$ in a water-saturated atmosphere.

In order to investigate the inhibitory activity of the compounds according to the invention the cells were "starved" for 16 hours, i.e. kept in culture medium without growth factors (ECGS+heparin). The cells were detached from the culture dishes using trypsin/EDTA and washed once in serum-containing medium. Then they were seeded out in amounts of $2.5 \times 10^3$ cells per well.

The proliferation of the cells was stimulated with 5 ng/ml of VEGF165 (vascular endothelial growth factor; H. Weich, GBF Braunschweig) and 10 µg/ml of heparin. As a control, 6 wells in each dish were not stimulated.

The compounds according to the invention were dissolved in 100% dimethylsulphoxide and added to the cultures in various dilutions as triple measurements, the maximum dimethylsulphoxide concentration being 0.3%.

The cells were incubated for 76 hours at 37° C., then for a further 16 hours $^3$H-thymidine (0.1 $\mu$Ci/well, Amersham) was added in order to determine the DNA synthesis. Then the radioactively labelled cells were immobilised on filter mats and the radioactivity incorporated was measured in a β-counter. In order to determine the inhibitory activity of the compounds according to the invention the mean value of the non-stimulated cells was subtracted from the mean value of the factor-stimulated cells (in the presence or absence of the compounds according to the invention).

The relative cell proliferation was calculated as a percentage of the control (HUVEC without inhibitor) and the concentration of active substance which inhibits the proliferation of the cells by 50% ($IC_{50}$) was determined.

The test results of the following compounds (a) to (f) of general formula I are provided by way of example:

(a) methyl 3-(Z)-[1-{4-[N-(2-dimethylamino-ethyl)-N-methyl-carbamoyl]-phenylamino}-1-phenyl-methylidene]-2-indolinone-6-carboxylate (b) methyl 3-(Z)-[1-{4-[N-(3-dimethylamino-propyl)-N-methyl-carbamoyl]-phenylamino}-1-phenyl-methylidene]-2-indolinone-6-carboxylate (c) methyl 3-(Z)-[1-{4-[(4-methyl-piperazin-1-yl)-carbonyl]-phenylamino}-1-phenyl-methylidene]-2-indolinone-6-carboxylate (d) methyl 3-(Z)-[1-{4-[(4-hydroxy-piperidin-1-yl)-carbonyl]-phenylamino}-1-phenyl-methylidene]-2-indolinone-6-carboxylate (e) methyl 3-(Z)-[1-{4-[(piperazin-1-yl)-carbonyl]-phenylamino}-1-phenyl-methylidene]-2-indolinone-6-carboxylate (f) methyl 3-(Z)-[1-{4-[N-(2-methylamino-ethyl)-N-methyl-carbamoyl]-phenylamino}-1-phenyl-methylidene]-2-indolinone-6-carboxylate (g) methyl 3-(Z)-[1-{4-[(4-dimethylamino-piperidin-1-yl)-carbonyl]-phenylamino}-1-phenyl-methylidene]-2-indolinone-6-carboxylate (h) methyl 3-(Z)-[1-{4-[(4-ethyl-piperazin-1-yl)-carbonyl]-phenylamino}-1-phenyl-methylidene]-2-indolinone-6-carboxylate (i) methyl 3-(Z)-[1-{4-[(4-(2-hydroxy-ethyl)-piperazin-1-yl)-carbonyl]-phenylamino}1-phenyl-methylidene]-2-indolinone-6-carboxylate (k) methyl 3-(Z)-{1-[4-(5-methyl-2,5-diaza-bicyclo[2.2.1]hept-2-yl-carbonyl)-phenylamino]-1-phenyl-methylidene}-2-indolinone-6-carboxylate The Table that follows contains the results found:

| compound | $IC_{50}$ [$\mu$M] |
|---|---|
| (a) | 0.04 |
| (b) | 0.02 |
| (c) | 0.03 |
| (d) | 0.05 |
| (e) | 0.01 |
| (f) | 0.01 |
| (g) | 0.01 |
| (h) | 0.02 |
| (i) | 0.02 |
| (k) | 0.01 |

In view of their inhibitory effect on the proliferation of cells, particularly endothelial cells and tumour cells, the compounds of general formula I are suitable for treating diseases in which the proliferation of cells, particularly endothelial cells, plays a part.

Thus, for example, the proliferation of endothelial cells and the concomitant neovascularisation constitute a crucial stage in tumour progression (Folkman J. et al., Nature 339, 58–61, (1989); Hanahan D. and Folkman J., Cell 86, 353–365, (1996)). Furthermore, the proliferation of endothelial cells is also important in haemangiomas, in metastasisation, rheumatoid arthritis, psoriasis and ocular neovascularisation (Folkman J., Nature Med. 1, 27–31, (1995)). The therapeutic usefulness of inhibitors of endothelial cell proliferation was demonstrated in the animal model for example by O'Reilly et al. and Parangi et al. (O'Reilly M. S. et al., Cell 88, 277–285, (1997); Parangi S. et al., Proc Natl Acad Sci USA 93, 2002–2007, (1996)).

The compounds of general formula I, their tautomers, their stereoisomers or the physiologically acceptable salts thereof are thus suitable for treating diseases or conditions characterized by excessive or anomalous cell proliferation, for example, for treating tumours (e.g. plate epithelial carcinoma, astrocytoma, Kaposi's sarcoma, glioblastoma, lung cancer, bladder cancer, neck carcinoma, melanoma, ovarian cancer, prostate cancer, breast cancer, small-cell lung cancer, glioma, colorectal cancer, urogenital cancer and gastrointestinal cancer as well as haematological cancers such as multiple myeloma), psoriasis, arthritis (e.g. rheumatoid arthritis), haemangioma, angiofibroma, eye diseases (e.g. diabetic retinopathy), neovascular glaucoma, kidney diseases (e.g. glomerulonephritis), diabetic retinopathy, malignant nephrosclerosis, thrombic microangiopathic syndrome, transplant rejections and glomerulopathy, fibrotic diseases (e.g. cirrhosis of the liver), mesangial cell proliferative diseases, arteriosclerosis, damage to the nerve tissue and for inhibiting the reocclusion of blood vessels after treatment with a balloon catheter, in vascular prosthetics or after the fitting of mechanical devices for holding the blood vessels open (e.g. stents), or other diseases in which cell proliferation or angiogenesis are involved.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastin, taxol), compounds which interact with nucleic acids (e.g. cisplatin, cyclophosphamide, adriamycin), hormone antagonists (e.g. tamoxifen), inhibitors of metabolic processes (e.g. 5-FU etc.), cytokines (e.g. interferons), kinase inhibitors, antibodies, or in conjunction with radiotherapy, etc. These combinations may be administered either simultaneously or sequentially.

For pharmaceutical use the compounds according to the invention are generally used for warm-blooded vertebrates, particularly humans, in doses of 0.01–100 mg/kg of body weight, preferably 0.1–20 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:
Preparation of the starting compounds:
Abbreviations used:
TBTU=O-(benzotriazol-1-yl)-N,N,N',N'-bis(tetramethylene-uronium-hexafluorophosphate
HOBt=1-hydroxy-1H-benzotriazole

EXAMPLE I

N-(2-dimethylamino-ethyl)-4-nitro-benzamide 1.25 ml of 2-(N,N-dimethylamino)-ethylamine are dissolved with 3 ml of triethylamine in 20 ml of methylene chloride and cooled to 0° C. Then 2 g of 4-nitrobenzoic acid chloride are added batchwise and the mixture is stirred for 5 min in the cold and for 20 min at ambient temperature. Finally, the precipitate is separated off by suction filtering and the organic phase is washed with water, dried over sodium sulphate and concentrated by rotary evaporation.

Yield: 1.8 g (70% of theoretical)

$R_f$ value: 0.78 (silica gel, methylene chloride/methanol=9:1)

$C_{11}H_{15}N_3O_3$

Mass spectrum: m/z=238 [M+H]$^+$

The following compounds are prepared analogously to Example I:
(1) N-(2-dimethylamino-ethyl)-N-methyl-4-nitro-benzamide
(2) N-(3-dimethylamino-propyl)-4-nitro-benzamide
(3) N-(3-dimethylamino-propyl)-N-methyl-4-nitro-benzamide
(4) N-(2-dimethylamino-ethyl)-N-ethyl-4-nitro-benzamide
(5) N-(2-(tert-butyloxycarbonyl-methylamino-ethyl)-N-methyl-4-nitro-benzamide
(6) N,N-bis-(2-diethylamino-ethyl)-4-nitro-benzamide
(7) N-(2-tert-butyloxycarbonyl-amino-ethyl)-4-nitro-benzamide
(8) N-(2-dimethylamino-ethyl)-3-nitro-benzamide
(9) N-(2-dimethylamino-ethyl)-N-methyl-3-nitro-benzamide
(10) N-(3-dimethylamino-propyl)-3-nitro-benzamide
(11) N-(3-dimethylamino-propyl)-N-methyl-3-nitro-benzamide
(12) 2-N-(dimethylamino-methyl)-carbamoyl-5-nitro-furan
(13) 4-(4-methyl-piperazin-1-yl-carbonyl)-nitrobenzene
(14) 4-(piperidin-1-yl-carbonyl)-nitrobenzene
(15) N-cyclohexyl-N-methyl-4-nitro-benzamide
(16) N-isopropyl-4-nitro-benzamide
(17) 4-(2,3,4,5-tetrahydro-1(H)-benzo[d]azepin-3-yl-carbonyl)-nitrobenzene
(18) 4-(4-hydroxy-piperidin-1-yl-carbonyl)-nitrobenzene
(19) 4-(4-tert-butyloxycarbonyl-piperazin-1-yl-carbonyl)-nitrobenzene
(20) 4-(4-tert-butyloxycarbonyl-[1,4]diazepan-1-yl-carbonyl)-nitrobenzene
(21) N-carbamoylmethyl-N-methyl-3-nitro-benzamide
(22) N-(2-methoxy-ethyl)-N-methyl-3-nitro-benzamide
(23) N-(2-carbamoylethyl)-3-nitro-benzamide
(24) N,N-(bis-(2-hydroxy-ethyl))-3-nitro-benzamide
(25) 4-(4-dimethylamino-piperidin-1-yl-carbonyl)-nitrobenzene
(26) 4-(4-ethyl-piperazin-1-yl-carbonyl)-nitrobenzene
(27) 4-(4-(2-dimethylamino-ethyl)-piperazin-1-yl-carbonyl)-nitrobenzene
(28) 4-(4-(2-hydroxy-ethyl)-piperazin-1-yl-carbonyl)-nitrobenzene
(29) 4-(5-methyl-2,5-diaza-bicyclo[2.2.1]hept-2-yl-carbonyl)-nitrobenzene
(30) 4-(4-tert-butyloxycarbonyl-trans-2,5-dimethyl-piperazin-1-yl-carbonyl)-nitrobenzene
(31) 4-(4-dimethylaminomethyl-piperidin-1-yl-carbonyl)-nitrobenzene
(32) 4-(cis-2,5-dimethyl-piperazin-1-yl-carbonyl)-nitrobenzene
(33) (R)-4-(3,4-dimethyl-piperazin-1-yl-carbonyl)-nitrobenzene
(34) 4-(4-(2-diethylamino-ethoxy)-piperidin-1-yl-carbonyl)-nitrobenzene
(35) 4-(3-(2-diethylamino-ethoxy)-pyrrolidin-1-yl-carbonyl)-nitrobenzene
(36) 4-(3-dimethylamino-pyrrolidin-1-yl-carbonyl)-nitrobenzene

EXAMPLE II

4-Nitro-1-methyl-2-[(2-dimethylamino-ethyl)-N-methyl-carbamoyl]-pyrrole 5.4 ml of 2-(N,N-dimethylamino)-ethylamine and 5.8 g of 1-methyl-4-nitro-pyrrol-2-carboxylic acid are dissolved in 200 ml of dimethylformamide and 5.7 ml of triethylamine, 13.1 g of TBTU and 5.5 g of HOBt are added. The mixture is stirred for 24 hours at ambient temperature. Finally, the solvent is substantially removed, water is added and the mixture is extracted with methylene chloride. The organic phase is dried over sodium sulphate and concentrated by rotary evaporation. The residue is purified on a silica gel column with methylene chloride/methanol/ammonia 8:2:0.1 as eluant.

Yield: 9.2 g (100% of theoretical)

$R_f$ value: 0.70 (silica gel, methylene chloride/methanol/ammonia=8:1:0.1)

$C_{11}H_{18}N_4O_3$

Mass spectrum: m/z=255 [M+H]$^+$

EXAMPLE III 4-amino-N-(2-dimethylamino-ethyl)-benzamide 1.8 g of N-(2-dimethylamino-ethyl)-4-nitro-benzamide are dissolved in 30 ml of methanol and hydrogenated over 0.2 g of palladium/charcoal at 50 psi of hydrogen for 2 hours at ambient temperature. The catalyst is filtered off and the filtrate is concentrated by rotary evaporation.

Yield: 1.5 g (95% of theoretical)

$R_f$ value: 0.38 (silica gel, methylene chloride/methanol=9:1)

$C_{11}H_{17}N_3O$

Mass spectrum: m/z=208 [M+H]$^+$

The following compounds are prepared analogously to Example III:
(1) 4-amino-N-(2-dimethylamino-ethyl)-N-methyl-benzamide
(2) 4-amino-N-(3-dimethylamino-propyl)-benzamide
(3) 4-amino-N-(3-dimethylamino-propyl)-N-methyl-benzamide
(4) 4-amino-N-(2-dimethylamino-ethyl)-N-ethyl-benzamide
(5) 4-amino-N-(2-(tert-butyloxycarbonyl-methylamino)-ethyl)-N-ethyl-benzamide
(6) 4-amino-N,N-bis-(2-diethylamino-ethyl)-benzamide
(7) 4-amino-N-(2-(tert-butyloxycarbonyl-amino)-ethyl)-benzamide (8) 3-amino-N-(2-dimethylamino-ethyl)-benzamide
(9) 3-amino-N-(2-dimethylamino-ethyl)-N-methyl-benzamide
(10) 3-amino-N-(3-dimethylamino-propyl)-benzamide
(11) 3-amino-N-(3-dimethylamino-propyl)-N-methyl-benzamide
(12) 5-amino-2-N-(dimethylamino-methyl)-carbamoyl-furan
(13) 4-(4-methyl-piperazin-1-yl-carbonyl)-aniline
(14) 4-(piperidin-1-yl-carbonyl)-aniline
(15) 4-amino-N-cyclohexyl-N-methyl-benzamide
(16) 4-amino-N-isopropyl-benzamide
(17) 4-(2,3,4,5-tetrahydro-1(H)-benzo[d]azepin-3-yl-carbonyl)-aniline
(18) 4-(4-hydroxy-piperidin-1-yl-carbonyl)-aniline
(19) 4-(4-tert-butyloxycarbonyl-piperazin-1-yl-carbonyl)-aniline
(20) 4-(4-tert-butyloxycarbonyl-[1,4]diazepan-1-yl-carbonyl)-aniline
(21) 3-amino-N-carbamoylmethyl-N-methyl-benzamide
(22) 3-amino-N-(2-methoxy-ethyl)-N-methyl-benzamide
(23) 3-amino-N-(2-carbamoylethyl)-benzamide
(24) 3-amino-N,N—(bis-(2-hydroxy-ethyl))-benzamide
(25) 4-amino-1-methyl-2-[(2-dimethylamino-ethyl)-N-methyl-carbamoyl]-pyrrole
(26) 4-(4-dimethylamino-piperidin-1-yl-carbonyl)-aniline
(27) 4-(4-ethyl-piperazin-1-yl-carbonyl)-aniline
(28) 4-(4-(2-dimethylamino-ethyl)-piperazin-1-yl-carbonyl)-aniline
(29) 4-(4-(2-hydroxy-ethyl)-piperazin-1-yl-carbonyl)-aniline
(30) 4-(5-methyl-2,5-diaza-bicyclo[2.2.1]hept-2-yl-carbonyl)-aniline
(31) 4-(4-tert-butyloxycarbonyl-trans-2,5-dimethyl-piperazin-1-yl-carbonyl)-aniline
(32) 4-(4-dimethylaminomethyl-piperidin-1-yl-carbonyl)-aniline
(33) 4-(cis-3,5-dimethyl-piperazin-1yl-carbonyl)-aniline
(34) (R)-4-(3,4-dimethyl-piperazin-1-yl-carbonyl)-aniline
(35) 4-(4-(2-diethylamino-ethoxy)-piperidin-1-yl-carbonyl)-aniline
(36) 4-(3-(2-diethylamino-ethoxy)-pyrrolidin-1-yl-carbonyl)-aniline
(37) 4-(3-dimethylamino -pyrrolidin-1-yl-carbonyl)-aniline

EXAMPLE IV

Methyl 4-methoxycarbonylmethyl-3-nitro-benzoate 54.3 g of methyl 3-nitro-benzoate and 29.0 g of methyl chloroacetate are dissolved in 100 ml of dimethylformamide and this solution is added dropwise at −10° C. to a solution of 78.5 g of potassium tert.butoxide in 500 ml of dimethylformamide. The mixture is stirred for another 10 minutes at ambient temperature and after this time the solution is poured onto 350 ml of concentrated hydrochloric acid in 2 l of iced water. The solution is stirred for 0.5 hours and the precipitate obtained is suction filtered and washed with water. The product is recrystallised from 150 ml of methanol and dried in vacuo at 40° C. Yield: 48.3 g (51% of theoretical), contains about 20% of methyl 6-methoxycarbonylmethyl-3-nitro-benzoate $R_f$ value: 0.7 (silica gel, petroleum ether/ethyl acetate=1:1)

Melting point: 65–73° C.

The following compound is prepared analogously to Example IV:

(1) ethyl 4-methoxycarbonylmethyl-3-nitro-benzoate Prepared from ethyl 4-methoxycarbonylmethyl-3-nitro-benzoate

EXAMPLE V

Methyl 2-indolinone-6-carboxylate 48.3 g of methyl 4-methoxycarbonylmethyl-3-nitro-benzoate are dissolved in 800 ml of concentrated acetic acid, 5.0 g of palladium on charcoal (10%) are added and the solution is hydrogenated for 2.5 hours at ambient temperature and 50 psi. The catalyst is filtered off and the filtrate is evaporated down. The residue is taken up in 150 ml of tert.-butylmethylether, filtered again and dried in vacuo at 100° C.

Yield: 28.6 g (98% of theoretical), $R_f$ value: 0.4 (silica gel, methylene chloride/methanol=10:1)

Melting point: 208–211° C.

The following compound is prepared analogously to Example V:

(1) ethyl 2-indolinone-6-carboxylate

Prepared from ethyl 4-methoxycarbonylmethyl-3-nitro-benzoate

EXAMPLE VI 1-acetyl-3-(1-ethoxy-1-phenylmethylene)-6-ethoxycarbonyl-2-indolinone 15.0 g of ethyl 2-indolinone-6-carboxylate, 49.6 ml of triethyl orthobenzoate and 150 ml of acetic anhydride are stirred for 4 hours at 110° C. After this time the solvent is removed, the residue is recrystallised from petroleum ether and dried in vacuo at 50° C.

Yield: 16.9 g (61% of theoretical), $R_f$ value: 0.5 (silica gel, petroleum ether/methylene chloride/ethyl acetate=5:4:1)

Melting point: 98–100° C.

$C_{22}H_{21}NO_5$

The following compound is prepared analogously to Example VI:

(1) 1-acetyl-3-(1-ethoxy-1-phenylmethylene)-6-methoxycarbonyl-2-indolinone Prepared from methyl 2-indolinone-6-carboxylate, triethyl orthobenzoate and acetic anhydride Preparation of the final compounds:

Example 1

Methyl 3-(Z)-[1-{4-[N-(2-dimethylamino-ethyl)-N-methyl-carbamoyl]-phenylamino}-1-phenyl-methylidene]-2-indolinone-6-carboxylate 0.3 g of 1-acetyl-3-(1-ethoxy-1-phenylmethylene)-6-methoxycarbonyl-2-indolinone and 0.2 g of 4-amino-N-(2-dimethylamino-ethyl)-N-methyl-benzamide are dissolved in 5 ml of dimethylformamide and stirred for 4 hours at 70° C. After cooling 3 ml of conc. ammonia are added and the mixture is stirred for another 30 minutes at ambient temperature. Then 1 ml of water is added, the precipitate formed is suction filtered, stirred with a little methanol and ether and then the solid substance is collected.

Yield: 0.1 g (24% of theoretical), $R_f$ value: 0.22 (silica gel, methylene chloride/methanol=9:1)

$C_{29}H_{30}N_4O_4$

Mass spectrum: m/z=499 [M+H]$^+$

The following compounds are prepared analogously to Example 1:

(1) methyl 3-(Z)-[1-{4-[(2-dimethylamino-ethyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-(2-dimethylamino-ethyl)-benzamide.

Yield: 0.15 g (36% of theoretical), $R_f$ value: 0.26 (silica gel, methylene chloride/methanol=9:1)

$C_{28}H_{28}N_4O_4$

Mass spectrum: m/z=483 [M-H]$^-$ (2) methyl 3-(Z)-[1-{4-[(3-dimethylamino-propyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-(3-dimethylamino-propyl)-benzamide.

Yield: 0.18 g (42% of theoretical)

$R_f$ value: 0.25 (silica gel, methylene chloride/methanol=9:1)

$C_{29}H_{30}N_4O_4$

Mass spectrum: m/z=497 [M-H]$^-$ (3) methyl 3-(Z)-[1-{4-[N-(3-dimethylamino-propyl)-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-(3-dimethylamino-propyl)-N-methyl-benzamide.

Yield: 0.18 g (41% of theoretical)

$R_f$ value: 0.22 (silica gel, methylene chloride/methanol=9:1)

$C_{30}H_{32}N_4O_4$

Mass spectrum: m/z=513 [M+H]$^+$ (4) methyl 3-(Z)-[1-{4-[(2-dimethylamino-ethyl)-N-ethyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-(2-dimethylamino-ethyl)-N-ethyl-benzamide.

Yield: 36% of theoretical $R_f$ value: 0.6 (silica gel, methylene chloride/methanol=4:1)

$C_{30}H_{32}N_4O_4$

Mass spectrum: m/z=513 [M+H]$^+$ (5) methyl 3-(Z)-[1-{4-[(2-(tert-butyloxycarbonyl-N-methylamino)-ethyl)-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-(2-(tert-butyloxycarbonyl-methylamino-ethyl)-N-ethyl-benzamide.

Yield: 25% of theoretical $R_f$ value: 0.8 (silica gel, methylene chloride/methanol=4:1)

$C_{33}H_{36}N_4O_6$

Mass spectrum: m/z=584 [M]$^+$ (6) methyl 3-(Z)-[1-{4-[N,N-bis-(2-diethylamino-ethyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-(N,N-bis-(2-diethylamino-ethyl)-benzamide.

Yield: 68% of theoretical $R_f$ value: 0.5 (silica gel, methylene chloride/methanol=4:1)

$C_{36}H_{45}N_5O_4$ (7) methyl 3-(Z)-[1-{3-[(2-dimethylamino-ethyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-(2-dimethylamino-ethyl)-benzamide.

Yield: 51% of theoretical, $R_f$ value: 0.6 (silica gel, methylene chloride/methanol=4:1)

$C_{28}H_{28}N_4O_4$

Mass spectrum: m/z=483 [M-H]$^-$ (8) methyl 3-(Z)-[1-{3-[(2-dimethylamino-ethyl)-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-(2-dimethylamino-ethyl)-N-methyl-benzamide.

Yield: 21% of theoretical, $R_f$ value: 0.35 (silica gel, methylene chloride/methanol=9:1)

$C_{29}H_{30}N_4O_4$

Mass spectrum: m/z=497 [M-H]$^-$ (9) methyl 3-(Z)-[1-{3-[(3-dimethylamino-propyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-(3-dimethylamino-propyl)-benzamide.

Yield: 53% of theoretical, $R_f$ value: 0.2 (silica gel, methylene chloride/methanol=4:1)

$C_{29}H_{30}N_4O_4$

Mass spectrum: m/z=497 [M-H]$^-$

(10) methyl 3-(Z)-[1-{3-[(3-dimethylamino-propyl)-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-(3-dimethylamino-propyl)-N-methyl-benzamide.

Yield: 25% of theoretical, $R_f$ value: 0.5 (silica gel, methylene chloride/methanol=4:1)

$C_{30}H_{32}N_4O_4$

Mass spectrum: m/z=513 [M+H]$^+$

(11) methyl 3-(Z)-[1-{4-[(4-methyl-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-methyl-piperazin-1-yl-carbonyl)-aniline.

Yield: 0.1 g (23% of theoretical),
Melting point: 196–197° C.
$C_{29}H_{28}N_4O_4$
Mass spectrum: m/z=495 [M–H]⁻

(12) methyl 3-(Z)-[1-{4-[(piperidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(piperidin-1-yl-carbonyl)-aniline.

Yield: 0.25 g (60% of theoretical),
Melting point: 268–269° C.
$C_{29}H_{27}N_3O_4$
Mass spectrum: m/z=480 [M–H]⁻

(13) methyl 3-(Z)-[1-{4-[N-cyclohexyl-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-cyclohexyl-N-methyl-benzamide.

Yield: 0.25 g (57% of theoretical),
Melting point: 263–265° C.
$C_{31}H_{31}N_3O_4$
Mass spectrum: m/z=508 [M–H]⁻

(14) methyl 3-(Z)-[1-{4-[isopropyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-isopropyl-benzamide.

Yield: 0.18 g (46% of theoretical),
Melting point: 273–274° C.
$C_{27}H_{25}N_3O_4$
Mass spectrum: m/z=454 [M–H]⁻

(15) methyl 3-(Z)-[1-{4-[2,3,4,5-tetrahydro-1 (H)-benzo[d]azepin-3-yl-carbonyl]-phenyl-amino}-1-phenyl-methylidene]-2-indolinone-6-carboxylate Prepared from 1-acetyl-3-(1-ethoxy-1-phenylmethylene)-6-methoxycarbonyl-2-indolinone and 4-(2,3,4,5-tetrahydro-1(H)-benzo[d]azepin-3-yl-carbonyl)-aniline.

Yield: 0.19 g (40% of theoretical),
Melting point: 278–279° C.
$C_{34}H_{29}N_3O_4$
Mass spectrum: m/z=542 [M–H]⁻

(16) methyl 3-(Z)-[1-{4-[(4-hydroxy-piperidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-hydroxy-piperidin-1-yl-carbonyl)-aniline.

Yield: 0.21 g (49% of theoretical),
Melting point: from 320° C. decomposition
$C_{29}H_{27}N_3O_5$
Mass spectrum: m/z=496 [M–H]⁻

(17) methyl 3-(Z)-[1-{4-[(4-tert-butyloxycarbonyl-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-tert-butyloxycarbonyl-piperazin-1-yl-carbonyl)-aniline.

Yield: 0.45 g (45% of theoretical),
Melting point: from 238° C. decomposition
$C_{33}H_{34}N_4O_6$
Mass spectrum: m/z=581 [M–H]⁻

(18) methyl 3-(Z)-[1-{4-[(4-tert-butyloxycarbonyl-[1,4]diazepan-1-yl)-carbonyl]-phenyl-amino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-tert-butyloxycarbonyl-[1,4]diazepan-1-yl-carbonyl)-aniline.

Yield: 0.58 g (56% of theoretical),
Melting point: from 213° C. decomposition
$C_{34}H_{36}N_4O_6$
Mass spectrum: m/z=595 [M–H]⁻

(19) methyl 3-(Z)-[1-(4-carbamoyl-phenylamino)-1-phenyl-methylidene]-2-indolinone-6-carboxylate Prepared from 1-acetyl-3-(1-ethoxy-1-phenylmethylene)-6-methoxycarbonyl-2-indolinone and 4-amino-benzamide.

Yield: 71% of theoretical
$R_f$ value: 0.5 (silica gel, methylene chloride/methanol=9:1)
$C_{24}H_{19}N_3O_4$
Mass spectrum: m/z=412 [M–H]⁻

(20) methyl 3-(Z)-[1-(4-propylcarbamoyl-phenylamino)-1-phenyl-methylidene]-2-indolinone-6-carboxylate Prepared from 1-acetyl-3-(1-ethoxy-1-phenylmethylene)-6-methoxycarbonyl-2-indolinone and 4-amino-N-propylbenzamide.

Yield: 56% of theoretical,
$R_f$ value: 0.4 (silica gel, methylene chloride/methanol=9:1)
$C_{27}H_{25}N_3O_4$
Mass spectrum: m/z=456 [M+H]⁺

(21) methyl 3-(Z)-[1-(4-dimethylcarbamoyl]-phenylamino)-1-phenyl-methylidene]-2-indolinone-6-carboxylate Prepared from 1-acetyl-3-(1-ethoxy-1-phenylmethylene)-6-methoxycarbonyl-2-indolinone and 4-amino-N,N-dimethylbenzamide.

Yield: 82% of theoretical,
$R_f$ value: 0.6 (silica gel, methylene chloride/methanol=9:1)
$C_{26}H_{23}N_3O_4$
Mass spectrum: m/z=440 [M–H]⁻

(22) methyl 3-(Z)-[1-{3-[N-(carbamoyl-methyl)-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-carbamoylmethyl-N-methyl-benzamide.

Yield: 39% of theoretical,
$R_f$ value: 0.35 (silica gel, methylene chloride/methanol=9:1)
$C_{27}H_{24}N_4O_5$
Mass spectrum: m/z=483 [M–H]⁻

(23) methyl 3-(Z)-[1-{3-[N-(2-methoxy-ethyl)-N-methyl-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-(2-methoxy-ethyl)-N-methyl-benzamide.

Yield: 59% of theoretical, $R_f$ value: 0.45 (silica gel, methylene chloride/methanol= 9:1)

$C_{28}H_{27}N_3O_5$

Mass spectrum: m/z=484 [M–H]⁻

(24) methyl 3-(Z)-[1-{3-[(2-carbamoyl-ethyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N-(2-carbamoylethyl)-benzamide.

Yield: 40% of theoretical, $R_f$ value: 0.35 (silica gel, methylene chloride/methanol= 9:1)

$C_{27}H_{24}N_4O_5$

Mass spectrum: m/z=483 [M–H]⁻

(25) methyl 3-(Z)-[1-{3-[N,N-bis-(2-hydroxy-ethyl)-carbamoyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 3-amino-N,N—(bis-(2-hydroxy-ethyl))-benzamide.

Yield: 67% of theoretical, $R_f$ value: 0.30 (silica gel, methylene chloride/methanol= 9:1)

$C_{28}H_{27}N_3O_6$

Mass spectrum: m/z=500 [M–H]⁻

(26) methyl 3-(Z)-[1-{1-methyl-2-[(2-dimethylamino-ethyl)-N-methyl-carbamoyl]-pyrrol-4-yl-amino}-1-phenyl-methylidene]-2-indolinone-6-carboxylate Prepared from 1-acetyl-3-(1-ethoxy-1-phenylmethylene)-6-methoxycarbonyl-2-indolinone and 4-amino-1-methyl-2-[(2-dimethylamino-ethyl)-N-methyl-carbamoyl]-pyrrole.

Yield: 77% of theoretical, $R_f$ value: 0.70 (silica gel, methylene chloride/methanol/ammonia=8:2:0,1)

$C_{28}H_{31}N_5O_4$

Mass spectrum: m/z=502 [M+H]⁺

(27) methyl 3-(Z)-[1-{4-[(4-dimethylamino-piperidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-dimethylamino-piperidin-1-yl-carbonyl)-aniline.

Yield: 57% of theoretical, $R_f$ value: 0.65 (silica gel, methylene chloride/methanol= 9:1)

$C_{31}H_{32}N_4O_4$

Mass spectrum: m/z=523 [M–H]⁻

(28) methyl 3-(Z)-[1-{4-[(4-ethyl-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-ethyl-piperazin-1-yl-carbonyl)-aniline.

Yield: 41% of theoretical, $R_f$ value: 0.30 (silica gel, methylene chloride/methanol= 9:1)

$C_{30}H_{30}N_4O_4$

Mass spectrum: m/z=511 [M+H]⁺

(29) methyl 3-(Z)-[1-{4-[(4-(2-dimethylamino-ethyl)-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-(2-dimethylamino-ethyl)-piperazin-1-yl-carbonyl)-aniline.

Yield: 31% of theoretical, $R_f$ value: 0.35 (silica gel, methylene chloride/methanol= 9:1)

$C_{32}H_{35}N_5O_4$

Mass spectrum: m/z=554 [M+H]⁺

(30) methyl 3-(Z)-[1-{4-[(4-(2-hydroxy-ethyl)-piperazin-1-yl)-carbonyl]-phenylamino}1-phenyl-methylidene]-2-indolinone-6-carboxylate Prepared from 1-acetyl-3-(1-ethoxy-1-phenylmethylene)-6-methoxycarbonyl-2-indolinone and 4-(4-(2-hydroxy-ethyl)-piperazin-1-yl-carbonyl)-aniline.

Yield: 78% of theoretical, $R_f$ value: 0.35 (silica gel, methylene chloride/methanol= 9:1)

$C_{30}H_{30}N_4O_5$

Mass spectrum: m/z=525 [M–H]⁻

(31) methyl 3-(Z)-{1-[4-(5-methyl-2,5-diaza-bicyclo[2.2.1]hept-2-yl-carbonyl)-phenylamino]-1-phenyl-methylidene}-2-indolinone-6-carboxylate Prepared from 1-acetyl-3-(1-ethoxy-1-phenylmethylene)-6-methoxycarbonyl-2-indolinone and 4-(5-methyl-2,5-diaza-bicyclo[2.2.1]hept-2-yl-carbonyl)-aniline.

Yield: 66% of theoretical, $R_f$ value: 0.25 (silica gel, methylene chloride/methanol/ammonia=9:1:0,1 [sic])

$C_{30}H_{28}N_4O_4$

Mass spectrum: m/z=509 [M+H]⁺

(32) methyl 3-(Z)-[1-{4-[(4-tert-butyloxycarbonyl-trans-2,5-dimethyl-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-tert-butyloxycarbonyl-trans-2,5-dimethyl-piperazin-1-yl-carbonyl)-aniline.

Yield: 63% of theoretical, $R_f$ value: 0.55 (silica gel, methylene chloride/methanol/ammonia=9:1:0,1 [sic])

$C_{35}H_{38}N_4O_6$

Mass spectrum: m/z=611 [M+H]⁺

(33) methyl 3-(Z)-[1-{4-[(4-dimethylaminomethyl-piperidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-dimethylaminomethyl-piperidin-1-yl-carbonyl)-aniline.

Yield: 10% of theoretical,

Melting point: 235–236° C.

$C_{32}H_{34}N_4O_4$

Mass spectrum: m/z=539 [M+H]⁺

(34) methyl 3-(Z)-[1-{4-[(cis-3,5-dimethyl-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(cis-3,5-dimethyl-piperazin-1-yl-carbonyl)-aniline.

Yield: 41% of theoretical,

Melting point: 265–266° C.

$C_{30}H_{30}N_4O_4$

Mass spectrum: m/z=511 [M+H]$^+$

(35) methyl (R)-3-(Z)-[1-{4-[(3,4-dimethyl-piperazin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and (R)-4-(3,4-dimethyl-piperazin-1-yl-carbonyl)-aniline.

Yield: 36% of theoretical,

Melting point: 265–266° C.

$C_{30}H_{30}N_4O_4$

Mass spectrum: m/z=511 [M+H]$^+$

(36) methyl 3-(Z)-[1-{4-[(4-(2-diethylamino-ethoxy)-piperidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(4-(2-diethylamino-ethoxy)-piperidin-1-yl-carbonyl)-aniline.

Yield: 12% of theoretical,

Melting point: 114° C.

$C_{35}H_{40}N_4O_5$

Mass spectrum: m/z=597 [M+H]$^+$

(37) methyl 3-(Z)-[1-{4-[(3-(2-diethylamino-ethoxy)-pyrrolidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(3-(2-diethylamino-ethoxy)-pyrrolidin-1-yl-carbonyl)-aniline.

Yield: 38% of theoretical,

Melting point: 133–134° C.

$C_{34}H_{38}N_4O_5$

Mass spectrum: m/z=583 [M+H]$^+$

(38) methyl 3-(Z)-[1-{4-[(3-dimethylamino-pyrrolidin-1-yl)-carbonyl]-phenylamino}-1-phenyl-methylidene]-2-indolinone-6-carboxylate Prepared from 1-acetyl-3-(1-ethoxy-1-phenylmethylene)-6-methoxycarbonyl-2-indolinone and 4-(3-dimethylamino-pyrrolidin-1-yl-carbonyl)-aniline.

Yield: 32% of theoretical,

Melting point: 259–260° C.

$C_{30}H_{30}N_4O_4$

Mass spectrum: m/z=511 [M+H]$^+$

Example 2

Methyl 3-(Z)-[1-{4-[(piperazin-1-yl)-carbonyl]-phenylamino}-1-phenyl-methylidene]-2-indolinone-6-carboxylate-trifluoroacetate A solution of 0.2 g (0.343 mmol) of methyl 3-(Z)-[1-{4-[(4-tert-butyloxycarbonyl-piperazin-1-yl)-carbonyl]-phenylamino}-1-phenyl-methylidene]-2-indolinone-6-carboxylate and 0.079 ml of trifluoroacetic acid in 20 ml of dichloromethane is stirred for 50 hours at ambient temperature. Then the solvent is distilled off in vacuo and the residue is combined with diisopropyl ether. The precipitate is filtered off and washed with diisopropyl ether.

Yield: 0.19 g (92% of theoretical),

Melting point: 270–271° C.

$C_{28}H_{26}N_4O_4$

Mass spectrum: m/z=483 [M+H]$^+$

The following compounds are prepared analogously to Example 2:

(1) methyl 3-(Z)-[1-{4-[([1,4]diazepan-1-yl)-carbonyl]-phenylamino}-1-phenyl-methylidene]-2-indolinone-6-carboxylate-trifluoroacetate A solution of 0.25 g (0.419 mmol) of methyl 3-(Z)-[1-{4-[(4-tert-butyloxycarbonyl-[1,4]diazepan-1-yl)-carbonyl]-phenylamino}-1-phenyl-methylidene]-2-indolinone-6-carboxylate and 0.4 ml of trifluoroacetic acid in 20 ml of dichloromethane is stirred for 48 hours at ambient temperature and for two hours at 45° C. The solvent is distilled off in vacuo and the residue is combined with diisopropyl ether. The precipitate is filtered off and washed with diisopropyl ether.

Yield: 0.23 g (89% of theoretical),

Melting point: 261–262° C.

$C_{29}H_{28}N_4O_4$

Mass spectrum: m/z=497 [M+H]$^+$ (2) methyl 3-(Z)-[1-{4-[N-(2-methylamino)-ethyl)-N-methyl-carbamoyl]-phenylamino}-1-phenyl-methylidene]-2-indolinone-6-carboxylate Prepared from methyl 3-(Z)-[1-{4-[(2-(tert-butyloxycarbonyl-methylamino)-ethyl)-N-methyl-carbonyl]-phenylamino}-1-phenyl-methylidene]-2-indolinone-6-carboxylate by treating with trifluoroacetic acid at ambient temperature in methylene chloride.

Yield: 86% of theoretical $R_f$ value: 0.5 (silica gel, methylene chloride/methanol= 4:1)

$C_{28}H_{28}N_4O_4$

Mass spectrum: m/z=485 [M+H]$^+$ (3) methyl 3-(Z)-[1-{4-[(trans-2,5-dimethyl-piperazin-1-yl)-carbonyl]-phenylamino}-1-phenyl-methylidene]-2-indolinone-6-carboxylate-trifluoroacetate Prepared from methyl 3-(Z)-[1-{4-[(4-tert-butyloxycarbonyl-trans-2,5-dimethyl-piperazin-1-yl)-carbonyl]-phenylamino}-1-phenyl-methylidene]-2-indolinone-6-carboxylate by treating with trifluoroacetic acid at ambient temperature in methylene chloride.

Yield: 100% of theoretical $R_f$ value: 0.4 (silica gel, methylene chloride/methanol/ammonia=9:1:0,1 [sic])

$C_{30}H_{30}N_4O_4$

Mass spectrum: m/z=511 [M+H]$^+$

Example 3

3-(Z)-[1-{4-[(4-methyl-piperazin-1-yl)-carbonyl]-phenylamino}-1-phenyl-methylidene]-2-indolinone-6-carboxylic acid 155 mg (310 mmol) of methyl 3-(Z)-[1-{4-[(4-methyl-piperazin-1-yl)-carbonyl]-phenylamino}-1-phenyl-methylidene]-2-indolinone-6-carboxylate are dissolved in 5 ml of methanol, 0.5 ml of 10N sodium hydroxide solution are added and the mixture is stirred for 8 hours at 50° C. Then the mixture is neutralised with dilute hydrochloric acid and water is added. The precipitate is filtered off and purified through an RP18-column with a gradient of acetonitrile and water as eluant.

Yield: 13 mg (9% of theoretical),
Melting point: 218° C.
$C_{28}H_{26}N_4O_4$
Mass spectrum: m/z=483 [M+H]$^+$ The following compounds may be prepared analogously to the foregoing Examples:

(1) methyl 3-(Z)-[1-{4-[N,N-bis-(2-dimethylamino-ethyl)-carbamoyl]-phenylamino}-1-phenyl-methylidene]-2-indolinone-6-carboxylate
(2) methyl 3-(Z)-[1-{4-[N,N-bis-(3-diethylamino-propyl)-carbamoyl]-phenylamino}-1-phenyl-methylidene]-2-indolinone-6-carboxylate
(3) methyl 3-(Z)-[1-{4-[(2-diethylamino-ethyl)-carbamoyl]-phenylamino}-1-phenyl-methylidene]-2-indolinone-6-carboxylate
(4) methyl 3-(Z)-[1-{4-[N,N-bis-(2-hydroxy-ethyl)-carbamoyl]-phenylamino}-1-phenyl-methylidene]-2-indolinone-6-carboxylate
(5) methyl 3-(Z)-[1-{4-[N-(carbamoyl-methyl)-N-methyl-carbamoyl]-phenylamino}-1-phenyl-methylidene]-2-indolinone-6-carboxylate
(6) methyl 3-(Z)-[1-{4-[(2-carbamoyl-ethyl)-carbamoyl]-phenylamino}-1-phenyl-methylidene]-2-indolinone-6-carboxylate
(7) methyl 3-(Z)-[1-{3-[N-(2-hydroxy-ethyl)-N-methyl-carbamoyl]-phenylamino}-1-phenyl-methylidene]-2-indolinone-6-carboxylate
(8) methyl 3-(Z)-[1-{3-[N-(2-methylamino-ethyl)-N-methyl-carbamoyl]-phenylamino}-1-phenyl-methylidene]-2-indolinone-6-carboxylate
(9) methyl 3-(Z)-[1-{3-[N(2-aminoethyl)-carbamoyl]-phenylamino}-1-phenyl-methylidene]-2-indolinone-6-carboxylate
(10) methyl 3-(Z)-[1-{4-[(2-(tert-butyloxycarbonyl-amino)-ethyl)-carbamoyl]-phenylamino}-1-phenyl-methylidene]-2-indolinone-6-carboxylate
(11) methyl 3-(Z)-[1-{5-[(2-dimethylamino-ethyl)-N-methyl-carbamoyl]-furan-2-yl-amino}-1-phenyl-methylidene]-2-indolinone-6-carboxylate
(12) methyl 3-(Z)-[1-{4-[(2-amino-ethyl)-carbamoyl]-phenylamino}-1-phenyl-methylidene]-2-indolinone-6-carboxylate
(13) methyl 3-(Z)-[1-{4-[(4-(2-dimethylamino-ethoxy)-piperidin-1-yl)-carbonyl]-phenylamino}-1-phenyl-methylidene]-2-indolinone-6-carboxylate
(14) methyl 3-(Z)-[1-{4-[(3-(2-dimethylamino-ethoxy)-pyrrolidin-1-yl)-carbonyl]-phenylamino}-1-phenyl-methylidene]-2-indolinone-6-carboxylate
(15) methyl (S)-3-(Z)-[1-{4-[(3,4-dimethyl-piperazin-1-yl)-carbonyl]-phenylamino}-1-phenyl-methylidene]-2-indolinone-6-carboxylate The compounds synthesised or capable of being synthesised according to Examples 1 and 2 are listed in Table 1.

TABLE 1

Compounds of general formula

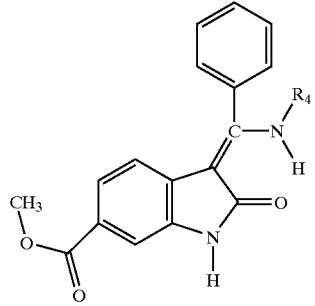

| Example | $R_4$ | $R_6$ |
|---|---|---|
| 1 | ―⟨phenyl⟩―$R_6$ | ―(C=O)―N(CH$_3$)―(CH$_2$)$_2$―N(CH$_3$)$_2$ |
| 1(1) | ―⟨phenyl⟩―$R_6$ | ―(C=O)―NH―(CH$_2$)$_2$―N(CH$_3$)$_2$ |
| 1(2) | ―⟨phenyl⟩―$R_6$ | ―(C=O)―NH―(CH$_2$)$_3$―N(CH$_3$)$_2$ |
| 1(3) | ―⟨phenyl⟩―$R_6$ | ―(C=O)―N(CH$_3$)―(CH$_2$)$_3$―N(CH$_3$)$_2$ |
| 1(4) | ―⟨phenyl⟩―$R_6$ | ―(C=O)―N(CH$_2$CH$_3$)―CH$_2$CH$_2$―N(CH$_3$)$_2$ |

TABLE 1-continued

Compounds of general formula

[Structure: 3-[(phenyl)(R4-NH)methylene]-6-(methoxycarbonyl)-2-oxo-indoline]

| Example | R$_4$ | R$_6$ |
|---|---|---|
| 1(5) | 4-R$_6$-phenyl | —(C=O)—N(CH$_3$)—CH$_2$CH$_2$—N(CH$_3$)—COOC(CH$_3$)$_3$ |
| 1(6) | 4-R$_6$-phenyl | —(C=O)—N[CH$_2$CH$_2$—N(CH$_2$CH$_3$)$_2$]$_2$ |
| 1(7) | 3-R$_6$-phenyl | —(C=O)—NH—CH$_2$CH$_2$—N(CH$_3$)$_2$ |
| 1(8) | 3-R$_6$-phenyl | —(C=O)—N(CH$_3$)—CH$_2$CH$_2$—N(CH$_3$)$_2$ |
| 1(9) | 3-R$_6$-phenyl | —(C=O)—NH—CH$_2$CH$_2$CH$_2$—N(CH$_3$)$_2$ |
| 1(10) | 3-R$_6$-phenyl | —(C=O)—N(CH$_3$)—CH$_2$CH$_2$CH$_2$—N(CH$_3$)$_2$ |
| 1(11) | 4-R$_6$-phenyl | 4-methylpiperazin-1-yl carbonyl |
| 1(12) | 4-R$_6$-phenyl | piperidin-1-yl carbonyl |

TABLE 1-continued

Compounds of general formula

[Structure: 3-[(phenyl)(R4-NH)methylene]-2-oxo-indoline-6-carboxylic acid methyl ester core]

| Example | R₄ | R₆ |
|---|---|---|
| 1(13) | —C₆H₄—R₆ (para) | —C(=O)—N(CH₃)(cyclohexyl) |
| 1(14) | —C₆H₄—R₆ (para) | —(C=O)—NH—CH(CH₃)₂ |
| 1(15) | —C₆H₄—R₆ (para) | —(C=O)—N(2,3,4,5-tetrahydro-1H-3-benzazepin-3-yl) |
| 1(16) | —C₆H₄—R₆ (para) | —(C=O)—N(4-hydroxypiperidin-1-yl) |
| 1(17) | —C₆H₄—R₆ (para) | —(C=O)—N(4-(tert-butoxycarbonyl)piperazin-1-yl) |
| 1(18) | —C₆H₄—R₆ (para) | —(C=O)—N(4-(tert-butoxycarbonyl)-1,4-diazepan-1-yl) |
| 1(19) | —C₆H₄—R₆ (para) | —(C=O)—NH₂ |
| 1(20) | —C₆H₄—R₆ (para) | —(C=O)—NH—CH₂CH₂CH₃ |

TABLE 1-continued

Compounds of general formula

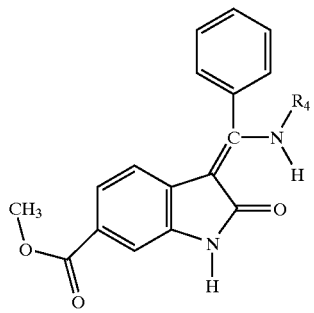

| Example | R$_4$ | R$_6$ |
|---|---|---|
| 1(21) | ![para-phenyl with R6] | —(C=O)—N(CH$_3$)$_2$ |
| 1(22) | ![meta-phenyl with R6] | —(C=O)—N(CH$_3$)—CH$_2$—(C=O)—NH$_2$ |
| 1(23) | ![meta-phenyl with R6] | —(C=O)—N(CH$_3$)—CH$_2$CH$_2$—OCH$_3$ |
| 1(24) | ![meta-phenyl with R6] | —(C=O)—NH—CH$_2$CH$_2$—CONH$_2$ |
| 1(25) | ![meta-phenyl with R6] | —(C=O)—N[CH$_2$CH$_2$—OH]$_2$ |
| 1(26) | ![N-methyl pyrrole with R6] | —(C=O)—N(CH$_3$)—CH$_2$CH$_2$—N(CH$_3$)$_2$ |
| 1(27) | ![para-phenyl with R6] | ![acetyl-piperidine-N(CH3)2] |
| 1(28) | ![para-phenyl with R6] | ![acetyl-piperazine-N-CH2CH3] |

TABLE 1-continued

Compounds of general formula

| Example | R₄ | R₆ |
|---|---|---|
| 1(29) | —⟨phenyl⟩—R₆ | —C(O)—N(piperazine)N—CH₂CH₂—N(CH₃)₂ |
| 1(30) | —⟨phenyl⟩—R₆ | —C(O)—N(piperazine)N—CH₂CH₂—OH |
| 1(31) | —⟨phenyl⟩—R₆ | —C(O)—(2,5-diazabicyclo)—N—CH₃ |
| 1(32) | —⟨phenyl⟩—R₆ | —C(O)—N(2,5-dimethylpiperazine)N—C(O)O—C(CH₃)₃ |
| 1(33) | —⟨phenyl⟩—R₆ | —C(O)—N(piperidine)—CH₂—N(CH₃)₂ |
| 1(34) | —⟨phenyl⟩—R₆ | —C(O)—N(3,5-dimethylpiperazine)NH |

TABLE 1-continued

Compounds of general formula

[Structure: 3-[(phenyl)(R4-NH)methylene]-6-(methoxycarbonyl)-2-oxo-2,3-dihydro-1H-indole core with R6 substituent]

| Example | R$_4$ | R$_6$ |
|---|---|---|
| 1(35) | –C$_6$H$_4$–R$_6$ (para) | –C(=O)–N(piperazine with 3,4-dimethyl, N4-CH$_3$, 3-CH$_3$) |
| 1(36) | –C$_6$H$_4$–R$_6$ (para) | –C(=O)–N(piperidin-1-yl)-4-(O–CH$_2$CH$_2$–N(CH$_2$CH$_3$)$_2$) |
| 1(37) | –C$_6$H$_4$–R$_6$ (para) | –C(=O)–N(pyrrolidin-1-yl)-3-(O–CH$_2$CH$_2$–N(CH$_2$CH$_3$)$_2$) |
| 1(38) | –C$_6$H$_4$–R$_6$ (para) | –C(=O)–N(pyrrolidin-1-yl)-3-N(CH$_3$)$_2$ |
| 2 | –C$_6$H$_4$–R$_6$ (para) | –C(=O)–N(piperazin-1-yl)–NH |
| 2(1) | –C$_6$H$_4$–R$_6$ (para) | –C(=O)–N(1,4-diazepan-1-yl)–NH |
| 2(2) | –C$_6$H$_4$–R$_6$ (para) | –(C=O)–N(CH$_3$)–CH$_2$CH$_2$–NH(CH$_3$) |

TABLE 1-continued

Compounds of general formula

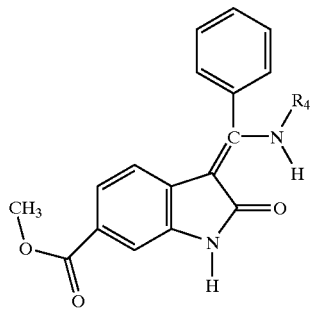

| Example | R$_4$ | R$_6$ |
|---|---|---|
| 2(3) | ―⟨C$_6$H$_4$⟩―R$_6$ (para) | ―C(=O)―N[(2S,5R)-2,5-dimethylpiperazin-1-yl] (acetyl on N1, NH on N4; 2,5-dimethyl) |
| (1) | ―⟨C$_6$H$_4$⟩―R$_6$ (para) | ―(C=O)―N[CH$_2$CH$_2$―N(CH$_3$)$_2$]$_2$ |
| (2) | ―⟨C$_6$H$_4$⟩―R$_6$ (para) | ―(C=O)―NH―CH$_2$CH$_2$CH$_2$―N(CH$_2$CH$_3$)$_2$ |
| (3) | ―⟨C$_6$H$_4$⟩―R$_6$ (para) | ―(C=O)―NH―CH$_2$CH$_2$―N(CH$_2$CH$_3$)$_2$ |
| (4) | ―⟨C$_6$H$_4$⟩―R$_6$ (para) | ―(C=O)―N(CH$_2$CH$_2$OH)$_2$ |
| (5) | ―⟨C$_6$H$_4$⟩―R$_6$ (para) | ―(C=O)―N(CH$_3$)―CH$_2$―(C=O)―NH$_2$ |
| (6) | ―⟨C$_6$H$_4$⟩―R$_6$ (para) | ―(C=O)―NH―CH$_2$CH$_2$―CONH$_2$ |
| (7) | ―⟨C$_6$H$_4$⟩―R$_6$ (meta) | ―(C=O)―N(CH$_3$)―CH$_2$CH$_2$―OH |
| (8) | ―⟨C$_6$H$_4$⟩―R$_6$ (meta) | ―(C=O)―N(CH$_3$)―CH$_2$CH$_2$―NH―CH$_3$ |

TABLE 1-continued

Compounds of general formula

[Structure: methyl 3-[(phenyl)(R4-NH)methylene]-2-oxo-2,3-dihydro-1H-indole-6-carboxylate core]

| Example | R₄ | R₆ |
|---------|----|----|
| (9) | 3-R₆-phenyl | —(C=O)—NH—CH₂CH₂—NH₂ |
| (10) | 4-R₆-phenyl | —(C=O)—NH—CH₂CH₂—NH—COOC(CH₃)₃ |
| (11) | 2,5-dimethylfuran-3-yl | —(C=O)—N(CH₃)—CH₂CH₂—N(CH₃)₂ |
| (12) | 4-R₆-phenyl | —(C=O)—NH—CH₂CH₂—NH₂ |
| (13) | 4-R₆-phenyl | —C(=O)—[1-piperidinyl-4-O—CH₂CH₂—N(CH₃)₂] |
| (14) | 4-R₆-phenyl | —C(=O)—[1-pyrrolidinyl-3-O—CH₂CH₂—N(CH₃)₂] |
| (15) | 4-R₆-phenyl | —C(=O)—[4-methyl-3-methylpiperazin-1-yl] |

Example 4

Dry Ampoule Containing 75 mg of Active Substance per 10 ml

| Composition: | |
|---|---|
| Active substance | 75.0 mg |
| Mannitol | 50.0 mg |
| water for injections | ad 10.0 ml |

Preparation:

Active substance and mannitol are dissolved in water. After packaging, the solution is freeze-dried. To produce the solution ready for use, the product is dissolved in water for injections.

Example 5

Dry Ampoule Containing 35 mg of Active Substance per 2 ml

| Composition: | |
|---|---|
| Active substance | 35.0 mg |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

Example 6

Tablet Containing 50 mg of Active Substance

| Composition: | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example 7

Tablet Containing 350 mg of Active Substance

| Composition: | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example 8

Capsules containing 50 mg of active substance

| Composition: | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

Example 9

Capsules containing 350 mg of active substance

| Composition: | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

Example 10

Suppositories containing 100 mg of active substance

| 1 suppository contains: | |
|---|---|
| Active substance | 100.0 mg |
| Polyethyleneglycol (M.W. 1500) | 600.0 mg |

-continued

| 1 suppository contains: | |
|---|---|
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of formula (I):

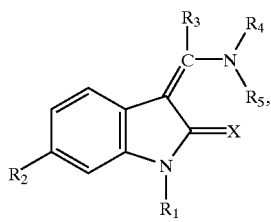

wherein

X denotes an oxygen or sulphur atom, $R_1$ denotes a hydrogen atom or a group which can be cleaved in vivo, $R_2$ denotes a carboxy group, a straight-chain or branched $C_{1-6}$-alkoxycarbonyl group, a $C_{4-7}$-cycloalkoxycarbonyl or an aryloxycarbonyl group, $R_3$ denotes a hydrogen atom, a $C_{1-6}$-alkyl, $C_{3-7}$-cycloalkyl, trifluoromethyl or heteroryl group, or a phenyl or naphthyl group, or a phenyl or naphthyl group each mono- or disubstituted by a fluorine, chlorine, bromine or iodine atom, by a trifluoromethyl, $C_{1-3}$-alkyl or $C_{1-3}$-alkoxy group, while in the event of disubstitution the substituents may be identical or different, $R_4$ denotes a phenyl, pyrrolyl or furanyl group, each substituted by $R_6$, which $R_4$ group may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and wherein $R_6$ denotes an aminocarbonyl, $C_{1-4}$-alkylamino-carbonyl, N—($C_{1-5}$-alkyl)-N—$C_{1-3}$-alkylamino-carbonyl, $C_{3-7}$-cycloalkylamino-carbonyl, N—($C_{1-5}$-alkyl)-N—$C_{3-7}$-cycloalkylaminocarbonyl, (phenyl-$C_{1-3}$-alkyl)aminocarbonyl, N—($C_{1-3}$-alkyl)-N-phenyl-$C_{1-3}$-alkylaminocarbonyl group, or a $C_{1-3}$-alkylaminocarbonyl or N—($C_{1-3}$-alkyl)-N—$C_{1-3}$-alkylaminocarbonyl group, wherein one or two alkyl moieties are substituted independently of one another by a nitro, cyano, carbamoyl, N—($C_{1-3}$-alkyl)-carbamoyl, di-N—($C_{1-3}$-alkyl)-carbamoyl, carboxy or $C_{1-3}$-alkoxycarbonyl group or are substituted in the 2- or 3-position by an amino ($C_{1-3}$-alkyl)-amino, di-($C_{1-3}$-alkyl)-amino, ($C_{1-4}$-alkoxycarbonyl)-amino, N—($C_{1-4}$-alkoxycarbonyl)-N—($C_{1-3}$-alkyl)-amino, piperazino, N—($C_{1-3}$-alkyl)-piperazino, a 4- to 7-membered cycloalkyleneimino group, a hydroxy or methoxy group, or a 4- to 7-membered cycloalkyleneiminocarbonyl group wherein the cycloalkylene moiety may be fused to a phenyl ring via two adjacent ring atoms or may form a bridge to a methylene or ethylene group via two non-adjacent ring atoms or one or two hydrogen atoms may each be replaced by a $C_{1-3}$-alkyl group and/or in each case the methylene group in the 4 position of a 6- or 7-membered cyclo-alkyleneiminocarbonyl group may be substituted by a carboxy, $C_{1-4}$-alkoxycarbonyl, aminocarbonyl, $C_{1-3}$-alkylaminocarbonyl, di-($C_{1-3}$-alkyl)-aminocarbonyl, di-($C_{1-3}$-alkyl)-amino-$C_{1-3}$-alkyl, di-($C_{1-3}$-alkyl)-amino, phenyl-$C_{1-3}$-alkylamino or N—($C_{1-3}$-alkyl)-N-phenyl-$C_{1-3}$-alkylamino group or a hydroxy or methoxy group or may be replaced by an oxygen or sulphur atom, by a sulphinyl, sulphonyl or —NH group or by a nitrogen atom which is substituted by a $C_{1-3}$-alkyl, phenyl, $C_{1-3}$-alkyl-carbonyl, $C_{1-4}$-alkoxy-carbonyl, di-($C_{1-3}$-alkyl)-amino-$C_{1-3}$-alkyl, ω-hydroxy-$C_{2-3}$-alkyl or benzoyl group, wherein all the single-bonded or fused phenyl groups contained in the $R_6$ groups may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by the term aryl in the aryloxycarbonyl group is meant a phenyl or naphthyl group, each optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and by the term heteroaryl group is meant a monocyclic 5- or 6-membered heteroary group optionally substituted in the carbon skeleton by a $C_{1-3}$-alkyl group, wherein the 6-membered heteroaryl group contains one, two or three ring nitrogen atoms and the 5-membered heteroaryl group contains a ring atom selected from an imino group optionally substituted by a $C_{1-3}$-alkyl or phenyl-$C_{1-3}$-alkyl group, an oxygen or sulphur atom or a ring atom selected from an imino group optionally substituted by a $C_{1-3}$-alkyl or phenyl-$C_{1-3}$-alkyl group or an oxygen or sulphur atom, and additionally a ring nitrogen atom or an imino ring atom group optionally substituted by a $C_{1-3}$-alkyl or phenyl-$C_{1-3}$-alkyl group and two ring nitrogen atoms, and wherein a phenyl ring may be fused to the above-mentioned monocyclic heteroaryl groups via two adjacent carbon atoms of the phenyl ring and via a nitrogen atom or via a carbon atom of the heteroaryl group, wherein the hydrogen atoms in the abovementioned alkyl and alkoxy groups or in any alkyl moieties contained in the above-defined groups $R_1$, $R_2$, $R_3$, $R_4$ or $R_5$ may be wholly or partly replaced by fluorine atoms, any saturated alkyl and alkoxy moieties containing more than 2 carbon atoms in the groups defined above also include the branched isomers thereof, and wherein a hydrogen atom of any carboxy group or a hydrogen atom bound to a nitrogen atom may each be replaced by a group which can be cleaved in vivo, or a tautomer, diastereomer, enantiomer, mixture thereof or a salt thereof, with the proviso that when $R_2$ denotes a carboxy group or a straight-chain or branched $C_{1-4}$-alkoxycarbonyl group, then $R_3$ does not denote a hydrogen atom, a $C_{1-6}$-alkyl, or a triftluoromethyl group.

2. A compound of formula I according to claim 1, wherein
X denotes an oxygen atom, $R_1$ denotes a hydrogen atom, a $C_{1-4}$-alkoxycarbonyl or $C_{2-4}$-alkanoyl group, $R_2$ denotes a carboxy group or a straight-chain or branched $C_{1-4}$-alkoxycarbonyl group, $R_3$ denotes a hydrogen atom, a $C_{1-6}$-alkyl or $C_{3-7}$-cycloalkyl group, or a phenyl or naphthyl group, or a phenyl or naphthyl group each mono- or disubstituted by a fluorine, chlorine or bromine atom, by a trifluoromethyl, $C_{1-3}$-alkyl or $C_{1-3}$-alkoxy group, while in the case of disubstitution the substituents ay be identical or different, $R_4$ denotes a furanyl group substituted by an aminocarbonyl, $C_{1-4}$-alkylaminocarbonyl or N—($C_{1-4}$-alkyl)-N—$C_{1-3}$-alkylaminocarbonyl group, wherein the $C_{1-4}$-alkyl-aminocarbonyl or N—($C_{1-4}$-alkyl)-N—$C_{1-3}$-alkylaminocarbonyl group each may be substituted at position 2 in one or both alkyl moieties by an amino, $C_{1-3}$-alkylamino or di-($C_{1-3}$-alkyl)amino group, or a pyrrolyl group substituted by an aminocarbonyl, $C_{1-4}$-alkylaminocarbonyl or N—($C_{1-4}$-alkyl)-N—$C_{1-3}$-alkylaminocarbonyl group, wherein the $C_{1-4}$-alkylaminocarbonyl or N—($C_{1-4}$-alkyl)-N—$C_{1-3}$-alkylaminocarbonyl group may each be substituted at position 2 in one or both alkyl moieties by an amino, $C_{1-3}$-alkylamino or di-($C_{1-3}$-alkyl)amino group and the nitrogen atom of the pyrrolyl ring is optionally substituted by a $C_{1-3}$-alkyl group, or a phenyl group substituted by the group $R_6$, which phenyl group may additionally be mono- or disubstituted by fluorine, chlorine or bromine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, while the substituents may be identical or different and wherein $R_6$ denotes an aminocarbonyl, $C_{1-4}$-alkylamino-carbonyl, N—($C_{1-5}$-alkyl)-N—$C_{1-3}$-alkyl-aminocarbonyl, $C_{3-7}$-cycloalkylamino-carbonyl, N—($C_{1-5}$-alkyl)-N—$C_{3-7}$-cycloalkyl-aminocarbonyl, (phenyl-$C_{1-3}$-alkyl)amino-carbonyl, N—($C_{1-3}$-alkyl)-N-phenyl-$C_{1-3}$-alkylamino-carbonyl group, or a $C_{1-3}$-alkylaminocarbonyl or N—($C_{1-3}$-alkyl)-N—$C_{1-3}$-alkylaminocarbonyl group, wherein one or two alkyl moieties are substituted independently of one a other by a nitro, cyano, carbamoyl, N—($C_{1-3}$-alkyl)-carbamoyl, di-N—($C_{1-3}$-alkyl)-carbamoyl, carboxy or $C_{1-3}$-alkoxycarbonyl group or are substituted in the 2- or 3-position by an amino, ($C_{1-3}$-alkyl)-amino, di-($C_{1-3}$-alkyl)-amino, ($C_{1-4}$-alkoxycarbonyl)-amino, N—($C_{1-4}$-alkoxycarbonyl)-N—($C_{1-3}$-alkyl)-amino, piperazino, N—($C_{1-3}$-alkyl)-piperazino, a piperazinyl or piperidinyl group, a hydroxy or methoxy group, or a 4- to 7-membered cycloalkyleneiminocarbonyl group wherein the cycloalkylene moiety may be fused to a phenyl ring via two adjacent ring atoms or two non-adjacent ring atoms may form a bridge to a methylene or ethylene group or one or two hydrogen atoms may each be replaced by a $C_{1-3}$-alkyl group and/or in each case the methylene group in the 4 position of a 6- or 7-membered cycloalkyleneiminocarbonyl group may be substituted by a carboxy, $C_{1-4}$-alkoxycarbonyl, aminocarbonyl, $C_{1-3}$-alkylaminocarbonyl, di-($C_{1-3}$-alkyl)-aminocarbonyl, di-($C_{1-3}$-alkyl)-amino-$C_{1-3}$-alkyl, di-($C_{1-3}$-alkyl)-amino, phenyl-$C_{1-3}$-alkylamino or $C_{1-3}$-alkyl)-N-phenyl-$C_{1-3}$-alkylamino group, a hydroxy or methoxy group, or may be replaced by an oxygen or sulphur atom, by a sulphinyl, sulphonyl or —NH group or by a nitrogen atom, which is substituted by a $C_{1-3}$-alkyl, phenyl, $C_{1-3}$-alkyl-carbonyl, $C_{1-4}$-alkoxy-carbonyl, di-($C_{1-3}$-alkyl)-amino-$C_{1-3}$-alkyl, ω-hydroxy-$C_{2-3}$-alkyl or benzoyl group, and $R_5$ denotes a hydrogen atom or a $C_{1-3}$-alkyl group, wherein the hydrogen atoms in the abovementioned alkyl and alkoxy groups or any alkyl moieties contained in the above-defined groups $R_1$, $R_2$, $R_3$, $R_4$ or $R_5$ may be wholly or partly replaced by fluorine atoms, any saturated alkyl and alkoxy moieties containing more than 2 carbon atoms in the groups defined above also include the branched isomers thereof, and wherein a hydrogen atom of any carboxy group or a hydrogen atom bound to a nitrogen atom may each be replaced by a group which can be cleaved in vivo, or a tautomer, diastereomer, enantiomer, mixture thereof or a salt thereof.

3. A compound of formula I according to claim 1, wherein

X denotes an oxygen atom, $R_1$ denotes a hydrogen atom, $R_2$ denotes a carboxy group or a $C_{1-2}$-alkoxycarbonyl group, $R_3$ denotes a phenyl or naphthyl group, or a phenyl group monosubstituted by a fluorine, chlorine or bromine atom, by a trifluoromethyl, $C_{1-3}$-alkyl or $C_{1-3}$-alkoxy group, $R_4$ denotes a pyrrolyl group substituted by an aminocarbonyl, $C_{1-4}$-alkylaminocarbonyl or N—($C_{1-4}$-alkyl)-N—$C_{1-3}$-alkylaminocarbonyl group, wherein the $C_{1-4}$-alkylaminocarbonyl or N—($C_{1-4}$-alkyl)-N—$C_{1-3}$-alkylaminocarbonyl group may be substituted at position 2 in one or both alkyl moieties by an amino, $C_{1-3}$-alkylamino or di-($C_{1-3}$-alkyl)amino group and the nitrogen atom of the pyrrolyl ring is optionally substituted by a $C_{1-3}$-alkyl group, or a phenyl group substituted in the 3- or 4-position by the group $R_6$, wherein $R_6$ denotes an aminocarbonyl, $C_{1-4}$-alkylamino-carbonyl, N—($C_{1-3}$-alkyl)-N—$C_{1-3}$-alkylamino-carbonyl, $C_{5-6}$-cycloalkylamino-carbonyl, N—($C_{1-5}$-alkyl)-N—$C_{5-6}$-cycloalkylaminocarbonyl group, or a $C_{1-3}$-alkylaminocarbonyl or N—($C_{1-3}$-alkyl)-N—$C_{1-3}$-alkylaminocarbonyl group, wherein one or two alkyl moieties are substituted independently of one another by a carbamoyl, N—($C_{1-3}$-alkyl)-carbamoyl, di-N—($C_{1-3}$-alkyl)-carbamoyl, $C_{1-3}$-alkoxycarbonyl group or are substituted in the 2- or 3-position by an amino, ($C_{1-3}$-alkyl)-amino, di-($C_{1-3}$-alkyl)-amino, ($C_{1-4}$-alkoxycarbonyl)-amino, N—($C_{1-4}$-alkoxycarbonyl)-N—($C_{1-3}$-alkyl)-amino, piperazino, N—($C_{1-3}$-alkyl)-piperazino, a piperazinyl or piperidinyl group, a hydroxy or methoxy group, or a piperidinocarbonyl, piperazinocarbonyl, homopiperazinocarbonyl or 2,3,4,5-tetrahydro-1(H)-azepino-carbonyl group, each of which may be fused to a phenyl ring via two adjacent unsubstitute carbon atoms or each may be substituted in the 4 position by a $C_{1-3}$-alkyl, $C_{1-4}$-alkoxycarbonyl, di-($C_{1-3}$-alkyl)-amino, di-($C_{1-3}$-alkyl)-amino-$C_{1-3}$-alkyl, 2-hydroxy-ethyl, hydroxy or methoxy group, or a 2,5-diaza-bicyclo[2.2.1]hept-2-yl-carbonyl group which may be substituted in the 5 position by a $C_{1-3}$-alkyl group, and $R_5$ denotes a hydrogen atom or a $C_{1-3}$-alkyl group, wherein the hydrogen atoms in the abovementioned methyl and methoxy groups may be replaced by 1, 2 or 3 fluorine atoms, and any saturated alkyl and alkoxy moieties containing more than 2 carbon atoms which are present in the groups defined above also include the branched isomers thereof, or a tautomer, diastereomer, enantiomer or mixture thereof or a salt thereof.

4. A compound of formula I according to claim 1, wherein

X denotes an oxygen atom, $R_1$ and $R_5$ each denote a hydrogen atom, $R_2$ denotes a methoxycarbonyl group, $R_3$ denotes a phenyl group and $R_4$ denotes a phenyl group which is monosubstituted in the 3- or 4-position by the group $R_6$, wherein $R_6$ denotes an aminocarbonyl, $C_{1-3}$-alkylamino-carbonyl, N—($C_{1-5}$-alkyl)-N—$C_{1-3}$-alkylamino-carbonyl, cyclohexylaminocarbonyl, N—($C_{1-5}$-alkyl)-N-cyclohexylaminocarbonyl, phenyl-$C_{1-3}$-alkylamino-carbonyl, N—($C_{1-3}$-alkyl)-N-phenyl-$C_{1-3}$-alkylamino-carbonyl, or a piperidinocarbonyl, 4-hydroxy-piperidinocarbonyl, 4-[di-($C_{1-3}$-alkyl)-amino]-piperidinocarbonyl, 4-[di-($C_{1-3}$-alkyl)-amino-$C_{1-3}$-alkyl]-piperidinocarbonyl, piperazinocarbonyl, N—($C_{1-3}$-alkyl)-piperazinocarbonyl, N—($C_{1-4}$-alkoxycarbonyl)-piperazinocarbonyl, N-[di-($C_{1-3}$-alkyl)-amino-$C_{1-3}$-alkyl]-piperazinocarbonyl, N-(2-hydroxy-ethyl)-piperazinocarbonyl, homopiperazinocarbonyl, N—($C_{1-3}$-alkyl)-homopiperazinocarbonyl, 2,3,4,5-tetrahydro-1(H)-benzo[d]azepino-carbonyl or 5-methyl-2,5-diaza-bicycl[2.2.1]hept-2-yl-carbonyl group, or a $C_{1-3}$-alkylaminocarbonyl or N—($C_{1-5}$-alkyl)-N—$C_{1-3}$-alkylaminocarbonyl group wherein one or two alkyl moieties are substituted by a carbarnoyl group or are substitute in the 2- or 3-position by an amino, ($C_{1-3}$-alkyl)-amino, di-($C_{1-3}$-alkyl)-amino, hydroxy or methoxy group, or a tautomer, diastereomer, enantiomer, or mixture thereof or a salt thereof.

5. A compound according to claim 1 which is:

(a) methyl 3-(Z)-[1-{4-[N-(2-dimethylamino-ethyl)-N-methyl-carbamoyl]-phenylamino}-1-phenyl-methylidene]-2-indolinone-6-carboxylate;

(b) methyl 3-(Z)-[1-{4-[N-(3-dimethylamino-propyl)-N-methyl-carbamoyl]-phenylamino}-1-phenyl-methylidene]-2-indolinone-6-carboxylate;

(c) methyl 3-(Z)-[1-{4-[(4-methyl-piperazin-1-yl)-carbonyl]-phenylamino}-1-phenyl-methylidene]-2-indolinone-6-carboxylate;

(d) methyl 3-(Z)-[1-{4-[(4-hydroxy-piperidin-1-yl)-carbonyl]-phenylamino}-1-phenyl-methylidene]-2-indolinone-6-carboxylate;

(e) methyl 3-(Z)-[1-{4-[(piperazin-1-yl)-carbonyl]-phenylamino}-1-phenyl-methylidene]-2-indolinone-6-carboxylate;

(f) methyl 3-(Z)-[1-{4-[N-(2-methylamino-ethyl)-N-methyl-carbamoyl]-phenylamino}-1-phenyl-methylidene]-2-indolinone-6-carboxylate;

(g) methyl 3-(Z)-[1-{4-[(4-dimethylamino-piperidin-1-yl)-carbonyl]-phenylamino}-1-phenyl-methylidene]-2-indolinone-6-carboxylate;

(h) methyl 3-(Z)-[1-{4-[(4-ethyl-piperazin-1-yl)-carbonyl]-phenylamino}-1-phenyl-methylidene]-2-indolinone-6-carboxylate;

(i) methyl 3-(Z)-[1-{4-[(4-(2-hydroxy-ethyl)-piperazin-1-yl)-carbonyl]-phenylamino}-1-phenyl-methylidene]-2-indolinone-6-carboxylate; or (j) methyl 3-(Z)-{1-[4-(5-methyl-2,5-diaza-bicyclo[2.2.1]hept-2-yl-carbonyl)-phenylamino]-1-phenyl-methylidene}-2-indolinone-6-carboxylate;

or a tautomer, mixture or salt thereof.

6. Methyl 3-(Z)-[1-{4-[(4-methyl-piperazin-1-yl)-carbonyl]-phenylamino}-1-phenyl-methylidene]-2-indolinone-6-carboxylate or a salt thereof.

7. A physiologically acceptable salt of a compound according to claim 1.

8. A pharmaceutical composition comprising a compound according to claim 1 optionally together with one or more inert carriers and/or diluents.

9. A method of treating a disease or condition characterized by excessive or anomalous endothelial cell proliferation in a patient comprising administering to said patient having said disease or condition an effective amount of a compound according to claim 1.

* * * * *